United States Patent
Queiroz et al.

(10) Patent No.: US 12,037,609 B2
(45) Date of Patent: Jul. 16, 2024

(54) NADH-DEPENDENT ENZYME MUTANTS TO CONVERT ACETONE INTO ISOPROPANOL

(71) Applicant: Braskem S.A., Sao Paulo (BR)

(72) Inventors: Verônica Leite Queiroz, Campinas (BR); Lucas Pedersen Parizzi, Campinas (BR); Iuri Estrada Gouvea, Campinas (BR); Debora Noma Okamoto, Votuporanga (BR); Rafael Victório Carvalho Guido, São Carlos (BR); Alessandro Silva Nascimento, São Carlos (BR); Igor Polikarpov, São Carlos (BR)

(73) Assignee: Braskem S.A., Sao Paulo (BR)

( * ) Notice: Subject to any disclaimer, the term of this patent is extended or adjusted under 35 U.S.C. 154(b) by 0 days.

(21) Appl. No.: 18/084,888

(22) Filed: Dec. 20, 2022

(65) Prior Publication Data

US 2023/0279365 A1 Sep. 7, 2023

Related U.S. Application Data

(62) Division of application No. 16/378,209, filed on Apr. 8, 2019, now Pat. No. 11,530,391.

(60) Provisional application No. 62/653,965, filed on Apr. 6, 2018.

(51) Int. Cl.
*C12N 9/04* (2006.01)
*C12N 1/21* (2006.01)
*C12N 15/52* (2006.01)

(52) U.S. Cl.
CPC ........... *C12N 9/0006* (2013.01); *C12N 15/52* (2013.01); *C12Y 101/01001* (2013.01)

(58) Field of Classification Search
None
See application file for complete search history.

(56) References Cited

U.S. PATENT DOCUMENTS

| | | | |
|---|---|---|---|
| 2008/0293125 A1 | 11/2008 | Subbian et al. | |
| 2010/0192985 A1 | 8/2010 | Aehle et al. | |
| 2010/0221800 A1* | 9/2010 | Liao | C12P 7/04 435/243 |
| 2013/0224838 A1 | 8/2013 | Koepke et al. | |
| 2013/0267006 A1* | 10/2013 | Koepke | C12N 9/0006 435/243 |
| 2017/0218417 A1 | 8/2017 | Ertl et al. | |
| 2017/0260551 A1* | 9/2017 | Koch | C12P 7/04 |

FOREIGN PATENT DOCUMENTS

WO 2009049274 A2 4/2009

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Maddock et al., Protein Eng. Des. Sel. 28:251-258, 2015 (Year: 2015).*
UniProt Database Accession No. P25984, Feb. 2017, 4 pages (Year: 2017).*
Yakov Korkhin, "Structural studies of two NADP-dependent bacterial alcohol dehydrogenases: structure, cofactor binding, origin of thermostability," Thesis, The Weizmann Institute of Science, Dec. 31, 1996 (Dec. 31, 1996), pp. 1-92 (92 pages).
International Search Report and Written Opinion for Application No. PCT/US19/26363, dated Jul. 10, 2019, 8 pages.
International Preliminary Report on Patentability for Application No. PCT/US19/26363, dated Jul. 10, 2019, 6 pages.
Extended European Search Report dated Dec. 3, 2021, for European counterpart Application No. 19782414.7 (7 Pages).
Oren Bogin et al., "Structural basis for the enhanced thermal stability of alcohol dehydrogenase mutants from the mesophilic bacterium Clostridium beijerinckii: contribution of salt bridging", Protein Science, Nov. 13, 2002 Nov. 13, 2002), vol. 11, No. 11, pp. 2561-2574, Tel Aviv, Israel, XP055101331, ISSN: 0961-8368, (14 pages). DOI: 10.1110/ ps.0222102.
Steve C. Schultz et al., PSite Saturation Mutagenesis of Active Site Residues of B-Lactamase, 1987, pp. 521-528, Plenum Press, New York (8 pages). https://doi.org/10.1007/978-1-4613-1787-6_53.
UniPrat Database Accession No. P75214, Feb. 2017, (2 pages).
UniPrat Database Accession No. Q92Z66, Mar. 2017, (2 pages).
Maddock et al., "Substitutions at the cofactor phosphate-binding site of a clostridial alcohol dehydrogenase lead to unexpected changes in substrate specificity," Protein Engineering, Design and Selection, vol. 28, Iss. 8, Jun. 1, 2015 (Jun. 1, 2015), pp. 251-258 (8 pages). doi: 10.1093/protein/gzv028.

* cited by examiner

Primary Examiner — David Steadman
(74) Attorney, Agent, or Firm — Morgan, Lewis & Bockius LLP

(57) ABSTRACT

The present disclosure relates to biological processes and systems for the production of isopropanol and/or acetone utilizing modified alcohol dehydrogenases that exhibit increased activity with NADH as a cofactor. The disclosure further relates to polynucleotides and polypeptides of the modified alcohol dehydrogenases, and host cells containing the polynucleotides and expressing the polypeptides.

20 Claims, 10 Drawing Sheets
Specification includes a Sequence Listing.

FIG. 1

| | NADH (acetone) | | | Acetone (NADH) | | |
|---|---|---|---|---|---|---|
| | kcat (min-1) | Km (mM) | kcat/Km (min-1 mM-1) | kcat (min-1) | Km (mM) | kcat/Km (min-1 mM-1) |
| C. beijerinckii G198D S199V P201E Y218A | 2.1 | 1.3 | 1.6 | 1.1 | 137.7 | 0.008 |
| C. autoethanogenum G198D S199V P201E Y218A | 29.3 | 2.7 | 10.9 | 70.8 | 28.4 | 2.5 |

FIG. 2

| | NADPH (acetone) | | | Acetone (NADPH) | | |
|---|---|---|---|---|---|---|
| | kcat (min-1) | Km (mM) | kcat/Km (min-1 mM-1) | kcat (min-1) | Km (mM) | kcat/Km (min-1 mM-1) |
| C. beijerinckii G198D S199V P201E Y218A | ND | ND | - | ND | ND | - |
| C. autoethanogenum G198D S199V P201E Y218A | 2.9 | 4.9 | 0.6 | 0.9 | 164 | 0.006 |

FIG. 3

| | NADH (acetone) | | | Acetone (NADH) | | |
|---|---|---|---|---|---|---|
| | kcat (min-1) | Km (mM) | kcat/Km (min-1 mM-1) | kcat (min-1) | Km (mM) | kcat/Km (min-1 mM-1) |
| G198E E247D | 39.28 | 0.37 | 106.25 | 115.00 | 8.43 | 13.64 |
| G198E E247N | 31.80 | 0.24 | 135.32 | 116.00 | 11.35 | 10.22 |
| I173L G198E | 46.32 | 0.58 | 80.00 | 100.00 | 11.11 | 9.00 |
| G198E Y218F E247D | NA | NA | NA | 73.53 | 10.05 | 7.32 |
| G198E T248V | NA | NA | NA | 87.48 | 5.66 | 15.46 |
| G198E E247Q | 110.00 | 1.80 | 61.11 | 65.00 | 13.00 | 5.00 |
| G198E | 35.89 | 3.19 | 11.25 | 70.83 | 28.47 | 2.49 |
| G198E Y218F | 45.38 | 2.27 | 20.02 | 44.07 | 20.60 | 2.14 |
| G198D Y218F | 46.61 | 2.74 | 17.01 | 38.23 | 18.89 | 2.02 |
| I173C G198E | 2.58 | 0.69 | 3.74 | 15.20 | 11.40 | 1.33 |

FIG. 4

| | NADPH (acetone) | | | Acetone (NADPH) | | |
|---|---|---|---|---|---|---|
| | kcat (min-1) | Km (mM) | kcat/Km (min-1 mM-1) | kcat (min-1) | Km (mM) | kcat/Km (min-1 mM-1) |
| G198E E247D | 6.00 | 0.45 | 13.45 | 22.70 | 65.90 | 0.34 |
| G198E E247N | 10.00 | 0.57 | 17.64 | NA | NA | NA |
| I173L G198E | 6.91 | 0.7 | 9.82 | 21.79 | 9.86 | 2.21 |
| G198E T248V | NA | NA | NA | 20.91 | 14.00 | 1.49 |
| G198E Y218F E247D | NA | NA | 8.11 | 22.7 | 65.9 | 0.34 |
| G198E E247Q | 9 | 1.11 | 0.66 | NO | NO | NO |
| G198E | 2.16 | 3.25 | 0.75 | 0.91 | 164.31 | 0.0055 |
| G198E Y218F | 1.74 | 2.33 | 1.54 | 2.56 | 2705.00 | 0.0009 |
| G198D Y218F | 3 | 1.95 | NO | NO | NO | NO |
| I173C G198E | NO | NO | NO | NA | NA | NA |

FIG. 5

| Mutants | NADH ACTIVITY | NADPH ACTIVITY |
|---|---|---|
| I173C G198E | YES | NO |
| I173L G198E | YES | YES |
| I173I G198E | NO | NO |
| I173T G198E | NO | NO |
| I173F G198E | YES | YES |
| G198E | YES | YES |
| G198E Y218F | YES | YES |
| G198E Y218P | YES | YES |
| G198E Y218A | YES | NO |
| G198E Y218W | YES | YES |
| G198E S199D | YES | NO |
| G198E S199I | YES | YES |
| G198E G244A | NO | NO |
| G198E G244L | YES | NO |
| G198E G244C | YES | NO |
| G198E G244M | NO | NA |
| G198E G244I | NO | NO |
| G198E G244F | NO | NA |
| G198E E247H | YES | YES |
| G198E E247D | YES | YES |
| G198E E247N | YES | YES |
| G198E E247Q | NO | NO |
| G198E F209L E247H | YES | YES |
| G198E Y218F E247D | NO | YES |
| G198E S199V P201E Y218A | NO | NO |
| G198E L294Y C295W | NO | YES |
| G198E Y267L L294Y C295W | NO | NO |
| G198E T248A | YES | NO |

| Mutants | NADH ACTIVITY | NADPH ACTIVITY |
|---|---|---|
| G198E T248M | YES | NO |
| G198E T248L | YES | YES |
| G198E T248V | YES | NO |
| I173C G198E E247Q | NO | NO |
| I173C G198E E247D | YES | YES |
| G198D | YES | NO |
| G198D S199I | YES | NO |
| G198D S199E | NO | NA |
| G198D S199G | YES | NO |
| G198D Y218F | YES | NO |
| G198D Y218P | YES | NO |
| G198D Y218W | YES | YES |
| G198D Y218A | YES | NO |
| G198D Y218F E247D | YES | NO |
| G198D S199V P201E Y218A | YES | NO |
| G198D S199V P201R | YES | NO |
| G198D E247Q | NO | NO |
| G198D E247D | YES | YES |
| G198D S199D | YES | YES |
| G198L S199E | NO | NO |
| G198L S199I | NO | NO |
| G198L S199D Y218D | NO | NO |
| G198L S199D Y218M | NO | NA |
| I175R G198L S199D | NO | NO |
| I175R G198L S199D Y218D | NO | NO |
| I175R G198L S199D Y218M | YES | YES |
| E247Q | NO | NO |
| G198E Y218F E247Q | NO | NO |
| I173C G198E E247Q | NO | NO |

FIG. 6

| # | Mutations |
|---|---|
| 1 | I173C G198E |
| 2 | I173L G198E |
| 3 | I173T G198E |
| 4 | I173F G198E |
| 5 | G198E |
| 6 | G198E Y218F |
| 7 | G198E Y218P |
| 8 | G198E Y218A |
| 9 | G198E Y218W |
| 10 | G198E S199D |
| 11 | G198E S199I |
| 12 | G198E G244A |
| 13 | G198E G244L |
| 14 | G198E G244C |
| 15 | G198E G244M |
| 16 | G198E G244I |
| 17 | G198E G244F |
| 18 | G198E E247H |
| 19 | G198E E247D |
| 20 | G198E E247N |
| 21 | G198E E247Q |
| 22 | G198E F209L E247H |
| 23 | G198E Y218F E247D |
| 24 | G198E S199V P201E Y218A |
| 25 | G198E L294Y C295W |
| 26 | G198E Y267L L294Y C295W |
| 27 | G198E T248A |
| 28 | G198E T248M |
| 29 | G198E T248L |
| 30 | G198E T248V |
| 31 | I173C G198E E247Q |
| 32 | I173C G198E E247D |
| 33 | G198D |
| 34 | G198D S199I |
| 35 | G198D S199E |
| 36 | G198D S199G |
| 37 | G198D Y218F |
| 38 | G198D Y218P |
| 39 | G198D Y218W |
| 40 | G198D Y218A |
| 41 | G198D Y218F E247D |
| 42 | G198D S199V P201E Y218A |
| 43 | G198D S199V P201R |
| 44 | G198D E247Q |
| 45 | G198D E247D |
| 46 | G198L S199D |
| 47 | G198L S199E |
| 48 | G198L S199D Y218D |
| 49 | G198L S199D Y218M |
| 50 | I175R G198L S199D |
| 51 | I175R G198L S199D Y218D |
| 52 | I175R G198L S199D Y218M |
| 53 | E247Q |
| 54 | G198E Y218F E247Q |
| 55 | I173C G198E E247Q |

| T38 | G198 | S199 | Y218 | I175 | I173 | R200 | P201 | C203 | G244 | E247 | T248 | K219 | G243 | Q251 | Y267 | L294 | C295 | K340 | K342 |
|---|---|---|---|---|---|---|---|---|---|---|---|---|---|---|---|---|---|---|---|
| H | D,E,G,K,N,R,S,A,V | D,G,H,I,L,N,R,S,V,C,M,P | P,A,D,F,I,N,S,T,V,Y,H,L | V,A | V,T,A,L,F,Y | R,G,S,N | P,E,D,K,S | R,K | A,C,M,F,I,W,L,H,P | D,N,Q,H | S,N,A,L,M,V | | | | | | | | |

FIG. 7

| Mutants |
| --- |
| I173C G198E |
| I173L G198E |
| G198E |
| G198E Y218F |
| G198E Y218P |
| G198E Y218A |
| G198E Y218W |
| G198E S199D |
| G198E S199I |
| G198E G244L |
| G198E G244C |
| G198E E247H |
| G198E E247D |
| G198E E247N |
| G198E E247Q |
| G198E Y218F E247D |
| G198E T248A |
| G198E T248M |
| G198E T248L |
| G198E T248V |
| I173C G198E E247D |
| G198D |
| G198D S199I |
| G198D S199G |
| G198D Y218F |
| G198D Y218P |
| G198D Y218W |
| G198D Y218A |
| G198D Y218F E247D |
| G198D S199V P201E Y218A |
| G198D S199V P201R |
| G198D E247D |
| G198L S199D |
| E247Q |

FIG. 8

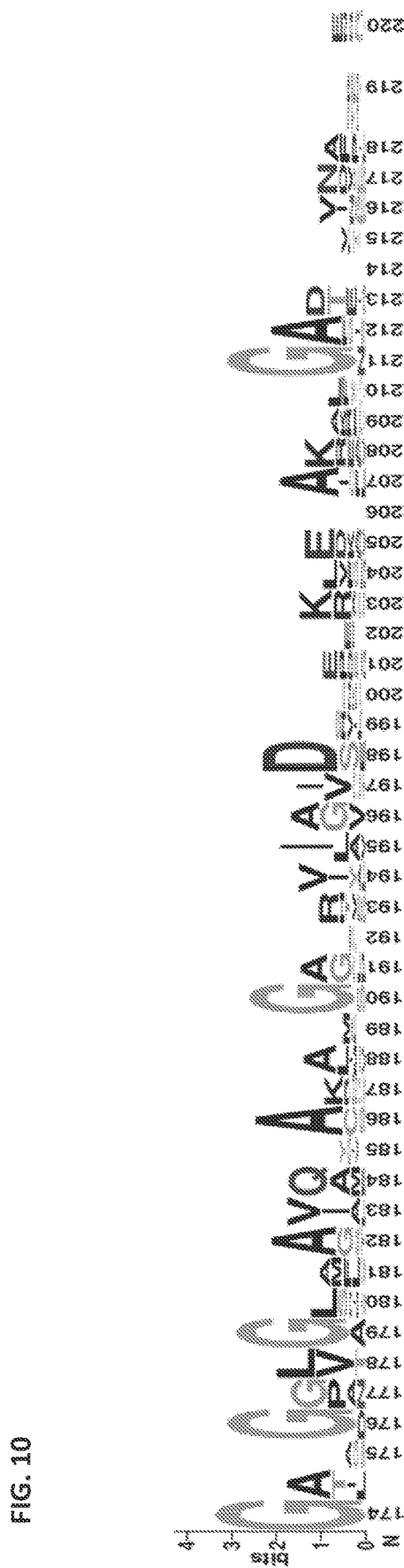

SEQUENCE LISTING

```
Sequence total quantity: 38
SEQ ID NO: 1            moltype = DNA  length = 1056
FEATURE                 Location/Qualifiers
source                  1..1056
                        mol_type = genomic DNA
                        organism = Clostridium beijerinckii
SEQUENCE: 1
atgaaagggt ttgccatgtt aggtatcaat aaactgggct ggattgaaaa agagcgcccg    60
gtggcgggtt catacgatgc aattgttcgt ccgctggccg tcagtccgtg caccagcgac   120
atccatacag tctttgaagg tgccctgggt gatcggaaaa acatgattct gggccatgaa   180
gccgtaggcg aagtagtgga agtgggcagc gaggtaaagg atttcaaacc gggtgatcgc   240
gtaattgttc cttgcacgac cccagattgg cgctcactgg aagttcaggc tggttttcag   300
cagcatagta acggtatgtt agcaggctgg aagtttagca attttaaaga cggggtgttc   360
ggggagtatt ttcatgtcaa cgatgcggac atgaatctgg ctattttacc taagagatatg   420
ccgctggaga acgcagtgat gattaccgac atgatgacga caggctttca cggtgcagaa   480
ctggctgaca tccaaatggg ctccagtgtg gtggttatcg gtattggtgc ggtcgggctg   540
atgggtatcg cgggcgcgaa attacggggc gctggtcgta tcatcggtgt cggcagccgt   600
ccaatttgcg ttgaagcagc taaattctat ggtgccacgg acattctgaa ctataaaaat   660
ggtcacatcg tcgatcaggt gatgaaactg accaatggca aaggtgtgga ccgcgtgatc   720
atggcgggcg gcggctcaga gactttatct caagcggtgt ctatgttaa acctggggc    780
atcattctca atattaacta tcatggctcc ggcgacgcat tactgatccc gcgtgttgaa   840
tggggctgtg ggatggccca caaaaccatt aaagggggt tatgtccggg tggtcgcctg    900
cgtgccgaaa tgctgcgtga catggtggtt tacaaccgtg tggatctgtc caaactggta   960
actcacgtat accacggttt cgatcacatt gaagaggcgc tgctgctgat gaaggataag   1020
ccaaaggatc tgattaaggc ggttgttatc ctgtaa                            1056

SEQ ID NO: 2            moltype = AA  length = 351
FEATURE                 Location/Qualifiers
source                  1..351
                        mol_type = protein
                        organism = Clostridium beijerinckii
SEQUENCE: 2
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVGSR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L           351

SEQ ID NO: 3            moltype = AA  length = 351
FEATURE                 Location/Qualifiers
REGION                  1..351
                        note = Modified ADH from Clostridium beijerinckii
source                  1..351
                        mol_type = protein
                        organism = synthetic construct
SEQUENCE: 3
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVCGIGAVGL   180
MGIAGAKLRG AGRIIGVGSR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L           351

SEQ ID NO: 4            moltype = AA  length = 351
FEATURE                 Location/Qualifiers
REGION                  1..351
                        note = Modified ADH from Clostridium beijerinckii
source                  1..351
                        mol_type = protein
```

```
                          organism = synthetic construct
SEQUENCE: 4
MKGFAMLGIN  KLGWIEKERP  VAGSYDAIVR  PLAVSPCTSD  IHTVFEGALG  DRKNMILGHE   60
AVGEVVEVGS  EVKDFKPGDR  VIVPCTTPDW  RSLEVQAGFQ  QHSNGMLAGW  KFSNFKDGVF  120
GEYFHVNDAD  MNLAILPKDM  PLENAVMITD  MMTTGFHGAE  LADIQMGSSV  VVIGIGAVGL  180
MGIAGAKLRG  AGRIIGVESR  PICVEAAKFY  GATDILNYKN  GHIVDQVMKL  TNGKGVDRVI  240
MAGGGSETLS  QAVSMVKPGG  IISNINYHGS  GDALLIPRVE  WGCGMAHKTI  KGGLCPGGRL  300
RAEMLRDMVV  YNRVDLSKLV  THVYHGFDHI  EEALLLMKDK  PKDLIKAVVI  L           351

SEQ ID NO: 5                moltype = AA  length = 351
FEATURE                     Location/Qualifiers
REGION                      1..351
                            note = Modified ADH from Clostridium beijerinckii
source                      1..351
                            mol_type = protein
                            organism = synthetic construct
SEQUENCE: 5
MKGFAMLGIN  KLGWIEKERP  VAGSYDAIVR  PLAVSPCTSD  IHTVFEGALG  DRKNMILGHE   60
AVGEVVEVGS  EVKDFKPGDR  VIVPCTTPDW  RSLEVQAGFQ  QHSNGMLAGW  KFSNFKDGVF  120
GEYFHVNDAD  MNLAILPKDM  PLENAVMITD  MMTTGFHGAE  LADIQMGSSV  VVIGIGAVGL  180
MGIAGAKLRG  AGRIIGVESR  PICVEAAKFY  GATDILNFKN  GHIVDQVMKL  TNGKGVDRVI  240
MAGGGSETLS  QAVSMVKPGG  IISNINYHGS  GDALLIPRVE  WGCGMAHKTI  KGGLCPGGRL  300
RAEMLRDMVV  YNRVDLSKLV  THVYHGFDHI  EEALLLMKDK  PKDLIKAVVI  L           351

SEQ ID NO: 6                moltype = AA  length = 351
FEATURE                     Location/Qualifiers
REGION                      1..351
                            note = Modified ADH from Clostridium beijerinckii
source                      1..351
                            mol_type = protein
                            organism = synthetic construct
SEQUENCE: 6
MKGFAMLGIN  KLGWIEKERP  VAGSYDAIVR  PLAVSPCTSD  IHTVFEGALG  DRKNMILGHE   60
AVGEVVEVGS  EVKDFKPGDR  VIVPCTTPDW  RSLEVQAGFQ  QHSNGMLAGW  KFSNFKDGVF  120
GEYFHVNDAD  MNLAILPKDM  PLENAVMITD  MMTTGFHGAE  LADIQMGSSV  VVIGIGAVGL  180
MGIAGAKLRG  AGRIIGVESR  PICVEAAKFY  GATDILNPKN  GHIVDQVMKL  TNGKGVDRVI  240
MAGGGSETLS  QAVSMVKPGG  IISNINYHGS  GDALLIPRVE  WGCGMAHKTI  KGGLCPGGRL  300
RAEMLRDMVV  YNRVDLSKLV  THVYHGFDHI  EEALLLMKDK  PKDLIKAVVI  L           351

SEQ ID NO: 7                moltype = AA  length = 351
FEATURE                     Location/Qualifiers
REGION                      1..351
                            note = Modified ADH from Clostridium beijerinckii
source                      1..351
                            mol_type = protein
                            organism = synthetic construct
SEQUENCE: 7
MKGFAMLGIN  KLGWIEKERP  VAGSYDAIVR  PLAVSPCTSD  IHTVFEGALG  DRKNMILGHE   60
AVGEVVEVGS  EVKDFKPGDR  VIVPCTTPDW  RSLEVQAGFQ  QHSNGMLAGW  KFSNFKDGVF  120
GEYFHVNDAD  MNLAILPKDM  PLENAVMITD  MMTTGFHGAE  LADIQMGSSV  VVIGIGAVGL  180
MGIAGAKLRG  AGRIIGVESR  PICVEAAKFY  GATDILNAKN  GHIVDQVMKL  TNGKGVDRVI  240
MAGGGSETLS  QAVSMVKPGG  IISNINYHGS  GDALLIPRVE  WGCGMAHKTI  KGGLCPGGRL  300
RAEMLRDMVV  YNRVDLSKLV  THVYHGFDHI  EEALLLMKDK  PKDLIKAVVI  L           351

SEQ ID NO: 8                moltype = AA  length = 351
FEATURE                     Location/Qualifiers
REGION                      1..351
                            note = Modified ADH from Clostridium beijerinckii
source                      1..351
                            mol_type = protein
                            organism = synthetic construct
SEQUENCE: 8
MKGFAMLGIN  KLGWIEKERP  VAGSYDAIVR  PLAVSPCTSD  IHTVFEGALG  DRKNMILGHE   60
AVGEVVEVGS  EVKDFKPGDR  VIVPCTTPDW  RSLEVQAGFQ  QHSNGMLAGW  KFSNFKDGVF  120
GEYFHVNDAD  MNLAILPKDM  PLENAVMITD  MMTTGFHGAE  LADIQMGSSV  VVIGIGAVGL  180
MGIAGAKLRG  AGRIIGVESR  PICVEAAKFY  GATDILNWKN  GHIVDQVMKL  TNGKGVDRVI  240
MAGGGSETLS  QAVSMVKPGG  IISNINYHGS  GDALLIPRVE  WGCGMAHKTI  KGGLCPGGRL  300
RAEMLRDMVV  YNRVDLSKLV  THVYHGFDHI  EEALLLMKDK  PKDLIKAVVI  L           351

SEQ ID NO: 9                moltype = AA  length = 351
FEATURE                     Location/Qualifiers
REGION                      1..351
                            note = Modified ADH from Clostridium beijerinckii
source                      1..351
                            mol_type = protein
                            organism = synthetic construct
SEQUENCE: 9
MKGFAMLGIN  KLGWIEKERP  VAGSYDAIVR  PLAVSPCTSD  IHTVFEGALG  DRKNMILGHE   60
AVGEVVEVGS  EVKDFKPGDR  VIVPCTTPDW  RSLEVQAGFQ  QHSNGMLAGW  KFSNFKDGVF  120
```

```
GEYFHVNDAD MNLAILPKDM PLENAVMITD MMTTGFHGAE LADIQMGSSV VVIGIGAVGL    180
MGIAGAKLRG AGRIIGVEDR PICVEAAKFY GATDILNYKN GHIVDQVMKL TNGKGVDRVI    240
MAGGGSETLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 10            moltype = AA   length = 351
FEATURE                  Location/Qualifiers
REGION                   1..351
                         note = Modified ADH from Clostridium beijerinckii
source                   1..351
                         mol_type = protein
                         organism = synthetic construct
SEQUENCE: 10
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVEIR PICVEAAKFY GATDILNYKN GHIVDQVMKL TNGKGVDRVI    240
MAGGGSETLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 11            moltype = AA   length = 351
FEATURE                  Location/Qualifiers
REGION                   1..351
                         note = Modified ADH from Clostridium beijerinckii
source                   1..351
                         mol_type = protein
                         organism = synthetic construct
SEQUENCE: 11
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGGGSETLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 12            moltype = AA   length = 351
FEATURE                  Location/Qualifiers
REGION                   1..351
                         note = Modified ADH from Clostridium beijerinckii
source                   1..351
                         mol_type = protein
                         organism = synthetic construct
SEQUENCE: 12
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGLGSETLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 13            moltype = AA   length = 351
FEATURE                  Location/Qualifiers
REGION                   1..351
                         note = Modified ADH from Clostridium beijerinckii
source                   1..351
                         mol_type = protein
                         organism = synthetic construct
SEQUENCE: 13
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGCGSETLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 14            moltype = AA   length = 351
FEATURE                  Location/Qualifiers
REGION                   1..351
                         note = Modified ADH from Clostridium beijerinckii
source                   1..351
                         mol_type = protein
                         organism = synthetic construct
SEQUENCE: 14
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGGGSDTLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351
```

```
SEQ ID NO: 15              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 15
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVESR PICVEAAKFY GATDILNYKN GHIVDQVMKL TNGKGVDRVI   240
MAGGGSNTLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 16              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 16
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVESR PICVEAAKFY GATDILNYKN GHIVDQVMKL TNGKGVDRVI   240
MAGGGSQTLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 17              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 17
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDSR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 18              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 18
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDIR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 19              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 19
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDGR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 20              moltype = AA   length = 351
FEATURE                    Location/Qualifiers
REGION                     1..351
```

```
                        note = Modified ADH from Clostridium beijerinckii
source                  1..351
                        mol_type = protein
                        organism = synthetic construct
SEQUENCE: 20
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDSR PICVEAAKFY GATDILNFKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 21           moltype = AA  length = 351
FEATURE                 Location/Qualifiers
REGION                  1..351
                        note = Modified ADH from Clostridium beijerinckii
source                  1..351
                        mol_type = protein
                        organism = synthetic construct
SEQUENCE: 21
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDSR PICVEAAKFY GATDILNPKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 22           moltype = AA  length = 351
FEATURE                 Location/Qualifiers
REGION                  1..351
                        note = Modified ADH from Clostridium beijerinckii
source                  1..351
                        mol_type = protein
                        organism = synthetic construct
SEQUENCE: 22
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDSR PICVEAAKFY GATDILNWKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 23           moltype = AA  length = 351
FEATURE                 Location/Qualifiers
REGION                  1..351
                        note = Modified ADH from Clostridium beijerinckii
source                  1..351
                        mol_type = protein
                        organism = synthetic construct
SEQUENCE: 23
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDSR PICVEAAKFY GATDILNAKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 24           moltype = AA  length = 351
FEATURE                 Location/Qualifiers
REGION                  1..351
                        note = Modified ADH from Clostridium beijerinckii
source                  1..351
                        mol_type = protein
                        organism = synthetic construct
SEQUENCE: 24
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTTGFHGAE LADIQMGSSV VVIGIGAVGL   180
MGIAGAKLRG AGRIIGVDVR EICVEAAKFY GATDILNAKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 25           moltype = AA  length = 351
FEATURE                 Location/Qualifiers
REGION                  1..351
                        note = Modified ADH from Clostridium beijerinckii
source                  1..351
                        mol_type = protein
                        organism = synthetic construct
```

```
SEQUENCE: 25
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTGFHGAE LADIQMGSSV VVIGIGAVGL    180
MGIAGAKLRG AGRIIGVDVR RICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 26              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 26
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTGFHGAE LADIQMGSSV VVIGIGAVGL    180
MGIAGAKLRG AGRIIGVLDR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 27              moltype = AA   length = 351
FEATURE                    Location/Qualifiers
REGION                     1..351
                           note = Modified ADH from Clostridium beijerinckii
source                     1..351
                           mol_type = protein
                           organism = synthetic construct
SEQUENCE: 27
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTGFHGAE LADIQMGSSV VVIGRGAVGL    180
MGIAGAKLRG AGRIIGVLDR PICVEAAKFY GATDILNDKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 28              moltype = AA   length = 351
FEATURE                    Location/Qualifiers
REGION                     1..351
                           note = Synthetic Sequence_Mutation I173C G198E E247D
source                     1..351
                           mol_type = protein
                           organism = synthetic construct
SEQUENCE: 28
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTGFHGAE LADIQMGSSV VVCGIGAVGL    180
MGIAGAKLRG AGRIIGVESR PICVEAAKFY GATDILNYKN GHIVDQVMKL TNGKGVDRVI   240
MAGGGSDTLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 29              moltype = AA   length = 351
FEATURE                    Location/Qualifiers
REGION                     1..351
                           note = Synthetic Sequence_Mutation I173L G198E
source                     1..351
                           mol_type = protein
                           organism = synthetic construct
SEQUENCE: 29
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTGFHGAE LADIQMGSSV VVLGIGAVGL    180
MGIAGAKLRG AGRIIGVESR PICVEAAKFY GATDILNYKN GHIVDQVMKL TNGKGVDRVI   240
MAGGGSETLS QAVSMVKPGG IISNINYHGS GDALLIPRVE WGCGMAHKTI KGGLCPGGRL   300
RAEMLRDMVV YNRVDLSKLV THVYHGFDHI EEALLLMKDK PKDLIKAVVI L            351

SEQ ID NO: 30              moltype = AA   length = 351
FEATURE                    Location/Qualifiers
REGION                     1..351
                           note = Synthetic Sequence_Mutation G198E E247H
source                     1..351
                           mol_type = protein
                           organism = synthetic construct
SEQUENCE: 30
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF   120
GEYFHVNDAD MNLAILPKDM PLENAVMITD MMTGFHGAE LADIQMGSSV VVIGIGAVGL    180
```

```
MGIAGAKLRG AGRIIGVESR PICVEAAKFY GATDILNYKN GHIVDQVMKL TNGKGVDRVI    240
MAGGGSHTLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 31           moltype = AA   length = 351
FEATURE                 Location/Qualifiers
REGION                  1..351
                        note = Synthetic Sequence_Mutation G198E Y218F E247D
source                  1..351
                        mol_type = protein
                        organism = synthetic construct
SEQUENCE: 31
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNFKN GHIVDQVMKL TNGKGVDRVI    240
MAGGGSDTLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 32           moltype = AA   length = 351
FEATURE                 Location/Qualifiers
REGION                  1..351
                        note = Synthetic Sequence_Mutation G198E T248A
source                  1..351
                        mol_type = protein
                        organism = synthetic construct
SEQUENCE: 32
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGGGSEALS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 33           moltype = AA   length = 351
FEATURE                 Location/Qualifiers
REGION                  1..351
                        note = Synthetic Sequence_Mutation G198E T248M
source                  1..351
                        mol_type = protein
                        organism = synthetic construct
SEQUENCE: 33
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGGGSEMLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 34           moltype = AA   length = 351
FEATURE                 Location/Qualifiers
REGION                  1..351
                        note = Synthetic Sequence_Mutation G198E T248L
source                  1..351
                        mol_type = protein
                        organism = synthetic construct
SEQUENCE: 34
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGGGSELLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351

SEQ ID NO: 35           moltype = AA   length = 351
FEATURE                 Location/Qualifiers
REGION                  1..351
                        note = Synthetic Sequence_Mutation G198E T248V
source                  1..351
                        mol_type = protein
                        organism = synthetic construct
SEQUENCE: 35
MKGFAMLGIN KLGWIEKERP VAGSYDAIVR PLAVSPCTSD IHTVFEGALG DRKNMILGHE    60
AVGEVVEVGS EVKDFKPGDR VIVPCTTPDW RSLEVQAGFQ QHSNGMLAGW KFSNFKDGVF    120
GEYFHVNDAD MNLAILPKDM PLENAVMITD MMTTGFHGAE LADIQMGSSV VVIGIGAVGL    180
MGIAGAKLRG AGRIIGVESR PICVEAAKFY GATDILNYKN GHIVDQVMKL TNGKGVDRVI    240
MAGGGSEVLS QAVSMVKPGG IISNINYHGS GDALLIPRVE WGCGMAHKTI KGGLCPGGRL    300
RAEMLRDMVV YNRVDLSKLV THVYHGFDHI EEALLLMKDK PKDLIKAVVI L             351
```

```
SEQ ID NO: 36              moltype = AA   length = 351
FEATURE                    Location/Qualifiers
REGION                     1..351
                           note = Synthetic Sequence_Mutation I173C Y218F E247D
source                     1..351
                           mol_type = protein
                           organism = synthetic construct
SEQUENCE: 36
MKGFAMLGIN KLGWIEKERP VAGSYDAIVR PLAVSPCTSD IHTVFEGALG DRKNMILGHE   60
AVGEVVEVGS EVKDFKPGDR VIVPCTTPDW RSLEVQAGFQ QHSNGMLAGW KFSNFKDGVF  120
GEYFHVNDAD MNLAILPKDM PLENAVMITD MMTTGFHGAE LADIQMGSSV VVCGIGAVGL  180
MGIAGAKLRG AGRIIGVGSR PICVEAAKFY GATDILNFKN GHIVDQVMKL TNGKGVDRVI  240
MAGGGSDTLS QAVSMVKPGG IISNINYHGS GDALLIPRVE WGCGMAHKTI KGGLCPGGRL  300
RAEMLRDMVV YNRVDLSKLV THVYHGFDHI EEALLLMKDK PKDLIKAVVI L          351

SEQ ID NO: 37              moltype = AA   length = 351
FEATURE                    Location/Qualifiers
REGION                     1..351
                           note = Synthetic Sequence_Mutation G198D E247D
source                     1..351
                           mol_type = protein
                           organism = synthetic construct
SEQUENCE: 37
MKGFAMLGIN KLGWIEKERP VAGSYDAIVR PLAVSPCTSD IHTVFEGALG DRKNMILGHE   60
AVGEVVEVGS EVKDFKPGDR VIVPCTTPDW RSLEVQAGFQ QHSNGMLAGW KFSNFKDGVF  120
GEYFHVNDAD MNLAILPKDM PLENAVMITD MMTTGFHGAE LADIQMGSSV VVIGIGAVGL  180
MGIAGAKLRG AGRIIGVDSR PICVEAAKFY GATDILNYKN GHIVDQVMKL TNGKGVDRVI  240
MAGGGSDTLS QAVSMVKPGG IISNINYHGS GDALLIPRVE WGCGMAHKTI KGGLCPGGRL  300
RAEMLRDMVV YNRVDLSKLV THVYHGFDHI EEALLLMKDK PKDLIKAVVI L          351

SEQ ID NO: 38              moltype = AA   length = 351
FEATURE                    Location/Qualifiers
REGION                     1..351
                           note = Synthetic Sequence_Mutation E247Q
source                     1..351
                           mol_type = protein
                           organism = synthetic construct
SEQUENCE: 38
MKGFAMLGIN KLGWIEKERP VAGSYDAIVR PLAVSPCTSD IHTVFEGALG DRKNMILGHE   60
AVGEVVEVGS EVKDFKPGDR VIVPCTTPDW RSLEVQAGFQ QHSNGMLAGW KFSNFKDGVF  120
GEYFHVNDAD MNLAILPKDM PLENAVMITD MMTTGFHGAE LADIQMGSSV VVIGIGAVGL  180
MGIAGAKLRG AGRIIGVGSR PICVEAAKFY GATDILNYKN GHIVDQVMKL TNGKGVDRVI  240
MAGGGSQTLS QAVSMVKPGG IISNINYHGS GDALLIPRVE WGCGMAHKTI KGGLCPGGRL  300
RAEMLRDMVV YNRVDLSKLV THVYHGFDHI EEALLLMKDK PKDLIKAVVI L          351
```

NADH-DEPENDENT ENZYME MUTANTS TO CONVERT ACETONE INTO ISOPROPANOL

CROSS-REFERENCE TO RELATED APPLICATIONS

This application is a divisional of U.S. application Ser. No. 16/378,209, filed Apr. 8, 2019, which claims the benefit of priority to U.S. Provisional Application No. 62/653,965, filed Apr. 6, 2018, each of which is hereby incorporated by reference in their entireties.

TECHNICAL FIELD

The present disclosure relates to biological processes and systems for creating and using mutant alcohol dehydrogenase enzymes exhibiting increased activity with NADH as a cofactor to prepare acetone or isopropanol.

STATEMENT REGARDING SEQUENCE LISTING

The sequence listing associated with this application is provided in XML format in lieu of a paper copy, and is hereby incorporated by reference into the specification. The name of the XML file containing the sequence listing is 127125_5010_US_01_Sequence_Listing.xml. The XML file is about 62,182 bytes, was created on May 30, 2023, and is being submitted electronically via Patent Center.

BACKGROUND

Metabolic pathways for fermentative production of isopropanol may make use of an NADPH-dependent secondary alcohol dehydrogenase to convert acetone to isopropanol. Within the metabolic pathways there is a positive net production of reduced nicotinamide adenine dinucleotide (NADH) and consumption of reduced nicotinamide adenine dinucleotide phosphate (NADPH). Both NADH and NADPH are essential electron donors in all organisms and the cellular pool of NADPH is lower than NADH. Considerable effort has been exerted on improving the NADPH pool in order to increase product yields dependent upon NADPH.

The present disclosure approaches the solution to increasing product yield in a different manner, by modifying the cofactor specificity of alcohol dehydrogenase to favor utilization of NADH over NADPH.

SUMMARY OF THE DISCLOSURE

In some embodiments, the disclosure is drawn to a nucleic acid construct comprising a polynucleotide sequence encoding a modified alcohol dehydrogenase, wherein the alcohol dehydrogenase exhibits activity with cofactor NADH as compared to an unmodified alcohol dehydrogenase; and wherein the polynucleotide sequence shares at least 85% sequence identity with SEQ ID NO:1.

In some embodiments, the modified alcohol dehydrogenase exhibits a cofactor preference for NADH over NADPH, as compared to an unmodified alcohol dehydrogenase. In some embodiments, the modified alcohol dehydrogenase exhibits an increased activity for reduction of acetone to isopropanol with NADH, as compared to an unmodified alcohol dehydrogenase. In some embodiments, the modified alcohol dehydrogenase exhibits an increased activity for oxidation of isopropanol to acetone, as compared to an unmodified alcohol dehydrogenase. In some embodiments, the modified alcohol dehydrogenase exhibits at least a 10 fold increase in activity with cofactor NADH as compared to an unmodified alcohol dehydrogenase.

In some embodiments, the modified alcohol dehydrogenase is a secondary alcohol dehydrogenase. In some embodiments, the modified alcohol dehydrogenase is NADH-dependent. In some embodiments, the modified alcohol dehydrogenase is a microbial alcohol dehydrogenase. In some embodiments, the microbial alcohol dehydrogenase is a bacterial alcohol dehydrogenase. In some embodiments, the bacterial alcohol dehydrogenase is a *Clostridium beijerinckii* alcohol dehydrogenase.

In some embodiments, the polynucleotide of the nucleic acid construct shares at least 90% sequence identity with SEQ ID NO:1. In some embodiments, the polynucleotide of the nucleic acid construct shares at least 95% sequence identity with SEQ ID NO:1. In some embodiments, the polynucleotide of the nucleic acid construct shares at least 99% sequence identity with SEQ ID NO:1

In some embodiments, the present disclosure is drawn to a polypeptide sequence comprising a modified alcohol dehydrogenase that exhibits activity with cofactor NADH as compared to an unmodified alcohol dehydrogenase; and wherein the modified alcohol dehydrogenase shares at least 85% sequence identity with SEQ ID NO:2. In some embodiments, the modified alcohol dehydrogenase exhibits a cofactor preference for NADH over NADPH, as compared to an unmodified alcohol dehydrogenase. In some embodiments, the modified alcohol dehydrogenase exhibits an increased activity for reduction of acetone to isopropanol with NADH, as compared to an unmodified alcohol dehydrogenase. In some embodiments, the modified alcohol dehydrogenase exhibits an increased activity for oxidation of isopropanol to acetone, as compared to an unmodified alcohol dehydrogenase. In some embodiments, the modified alcohol dehydrogenase exhibits at least a 10 fold increase in activity with cofactor NADH as compared to an unmodified alcohol dehydrogenase.

In some embodiments, the modified alcohol dehydrogenase is a secondary alcohol dehydrogenase. In some embodiments, the modified alcohol dehydrogenase is NADH-dependent. In some embodiments, the modified alcohol dehydrogenase is a microbial alcohol dehydrogenase. In some embodiments, the microbial alcohol dehydrogenase is a bacterial alcohol dehydrogenase. In some embodiments, the bacterial alcohol dehydrogenase is a *Clostridium beijerinckii* alcohol dehydrogenase.

In some embodiments, the polypeptide sequence comprises a signal peptide. In some embodiments, the signal peptide is a secretion signal.

In some embodiments, the modified alcohol dehydrogenase shares at least 90% sequence identity with SEQ ID NO:2. In some embodiments, the modified alcohol dehydrogenase shares at least 95% sequence identity with SEQ ID NO:2. In some embodiments, the modified alcohol dehydrogenase shares at least 99% sequence identity with SEQ ID NO:2.

In some embodiments, the modified alcohol dehydrogenase sequence is selected from SEQ ID NOs: 3-38.

In some embodiments, the modified alcohol dehydrogenase sequence comprises an amino acid substitution at one or more of the following residues: T38, G198, S199, Y218, I175, I173, R200, P201, C203, G244, E247, T248, K219, G243, Q251, Y267, L294, C295, K340, and K342.

In some embodiments, the modified alcohol dehydrogenase sequence comprises an amino acid substitution at residue T38 with an H amino acid residue. In some embodiments, the modified alcohol dehydrogenase sequence comprises an amino acid substitution at residue G198 with a D, E, G, K, N, R, S, A, or V amino acid residue. In some embodiments, the modified alcohol dehydrogenase sequence comprises an amino acid substitution at residue S199 with a D, G, H, I, L, N, R, S, V, C, M, or P amino acid residue. In some embodiments, wherein the modified alcohol dehydrogenase sequence comprises an amino acid substitution at residue Y218 with a P, A, D, F, I, N, S, T, V, H, L, or Y amino acid residue. In some embodiments, the modified alcohol dehydrogenase sequence comprises an amino acid substitution at residue I173 with a V, T, A, L, F, or Y amino acid residue. In some embodiments, the modified alcohol dehydrogenase sequence comprises an amino acid substitution at residue I175 with a V or A amino acid residue. In some embodiments, the modified alcohol dehydrogenase sequence comprises an amino acid substitution at residue R200 with a R, G, S, or N amino acid residue. In some embodiments, the modified alcohol dehydrogenase sequence comprises an amino acid substitution at residue P201 with a P, E, D, K, or S amino acid residue. In some embodiments, the modified alcohol dehydrogenase sequence comprises an amino acid substitution at residue C203 with an R or K amino acid residue. In some embodiments, the modified alcohol dehydrogenase sequence comprises an amino acid substitution at residue G244 with an A, C, M, F, I, W, L, H, or P amino acid residue. In some embodiments, the modified alcohol dehydrogenase sequence comprises an amino acid substitution at residue E247 with a D, N, Q, or H amino acid residue. In some embodiments, the modified alcohol dehydrogenase sequence comprises an amino acid substitution at residue T248 with an S, N, A, L, M, or V amino acid residue.

In some embodiments, the modified alcohol dehydrogenase sequence comprises one or more of the following amino acid substitutions: G198E, E247Q, E247D, E247N, Y218F, G198D, I173C, G198L, S199D, Y218P, or Y218A.

In some embodiments, the modified alcohol dehydrogenase sequence comprises G198E and E247Q amino acid substitutions. In some embodiments, the modified alcohol dehydrogenase sequence comprises a G198E amino acid substitution. In some embodiments, the modified alcohol dehydrogenase sequence comprises G198E and Y218F amino acid substitutions. In some embodiments, the modified alcohol dehydrogenase sequence comprises G198E and E247D amino acid substitutions. In some embodiments, the modified alcohol dehydrogenase sequence comprises G198E and E247N amino acid substitutions. In some embodiments, the modified alcohol dehydrogenase sequence comprises G198D and Y218F amino acid substitutions. In some embodiments, the modified alcohol dehydrogenase sequence comprises I173C and G198E amino acid substitutions. In some embodiments, the modified alcohol dehydrogenase sequence comprises a G198D amino acid substitution. In some embodiments, the modified alcohol dehydrogenase sequence comprises G198L and S199D amino acid substitutions. In some embodiments, the modified alcohol dehydrogenase sequence comprises G198D and Y218P amino acid substitutions. In some embodiments, the modified alcohol dehydrogenase sequence comprises G198E and Y218P amino acid substitutions. In some embodiments, the modified alcohol dehydrogenase sequence comprises G198D and Y218A amino acid substitutions.

In some embodiments, the specification is drawn to a recombinant microorganism comprising a nucleic acid construct of the present disclosure.

In some embodiments, the present disclosure is drawn to a method of producing a recombinant microorganism that produces a modified alcohol dehydrogenase that exhibits activity with cofactor NADH as compared to an unmodified alcohol dehydrogenase, the method comprising introducing a polynucleotide sequence encoding a polypeptide sequence of the present disclosure into a microorganism.

In some embodiments, the microorganism is a bacterium. In some embodiments, the bacterium is a species of *Escherichia* or *Bacillus*. In some embodiments, the bacterium is *Escherichia coli*. In some embodiments, the microorganism is a fungus. In some embodiments, the fungus is a yeast. In some embodiments, the fungus is a species of *Saccharomyces*, *Pichia*, or *Aspergillus*.

In some embodiments of the method, the modified alcohol dehydrogenase exhibits a cofactor preference for NADH over NADPH, as compared to an unmodified alcohol dehydrogenase.

In some embodiments, the present disclosure is drawn to a recombinant microorganism expressing a polypeptide sequence comprising a modified alcohol dehydrogenase that exhibits activity with cofactor NADH as compared to an unmodified alcohol dehydrogenase; and wherein the modified alcohol dehydrogenase shares at least 85% sequence identity with SEQ ID NO:2. In some embodiments of the recombinant microorganism, the modified alcohol dehydrogenase exhibits a cofactor preference for NADH over NADPH, as compared to an unmodified alcohol dehydrogenase. In some embodiments of the recombinant microorganism, the modified alcohol dehydrogenase exhibits an increased activity for reduction of acetone to isopropanol, as compared to an unmodified alcohol dehydrogenase. In some embodiments of the recombinant microorganism, the modified alcohol dehydrogenase exhibits an increased activity for oxidation of isopropanol to acetone, as compared to an unmodified alcohol dehydrogenase. In some embodiments of the recombinant microorganism, the modified alcohol dehydrogenase exhibits at least a 10 fold increase in activity with cofactor NADH as compared to an unmodified alcohol dehydrogenase.

In some embodiments of the recombinant microorganism, the modified alcohol dehydrogenase is a secondary alcohol dehydrogenase. In some embodiments of the recombinant microorganism, the modified alcohol dehydrogenase is NADH-dependent. In some embodiments of the recombinant microorganism, the modified alcohol dehydrogenase is a microbial alcohol dehydrogenase. In some embodiments of the recombinant microorganism, the microbial alcohol dehydrogenase is a bacterial alcohol dehydrogenase. In some embodiments of the recombinant microorganism, the bacterial alcohol dehydrogenase is a *Clostridium bejerinckii* alcohol dehydrogenase.

In some embodiments of the recombinant microorganism, the polypeptide sequence comprises a signal peptide. In some embodiments of the recombinant microorganism, the signal peptide is a secretion signal.

In some embodiments of the recombinant microorganism, the modified alcohol dehydrogenase shares at least 90% sequence identity with SEQ ID NO:2. In some embodiments of the recombinant microorganism, the modified alcohol dehydrogenase shares at least 95% sequence identity with SEQ ID NO:2. In some embodiments of the recombinant microorganism, the modified alcohol dehydrogenase shares at least 99% sequence identity with SEQ ID NO:2.

In some embodiments of the recombinant microorganism, the modified alcohol dehydrogenase sequence is selected from SEQ ID NOs: 3-38.

In some embodiments of the recombinant microorganism, the modified alcohol dehydrogenase sequence comprises an amino acid substitution at one or more of the following residues: T38, G198, S199, Y218, I175, I173, R200, P201, C203, G244, E247, T248, K219, G243, Q251, Y267, L294, C295, K340, and K342.

In some embodiments of the recombinant microorganism, the modified alcohol dehydrogenase sequence comprises an amino acid substitution at residue T38 with an H amino acid residue. In some embodiments of the recombinant microorganism, the modified alcohol dehydrogenase sequence comprises an amino acid substitution at residue G198 with a D, E, G, K, N, R, S, A, or V amino acid residue. In some embodiments of the recombinant microorganism, the modified alcohol dehydrogenase sequence comprises an amino acid substitution at residue S199 with a D, G, H, I, L, N, R, S, V, C, M, or P amino acid residue. In some embodiments of the recombinant microorganism, wherein the modified alcohol dehydrogenase sequence comprises an amino acid substitution at residue Y218 with a P, A, D, F, I, N, S, T, V, H, L, or Y amino acid residue. In some embodiments of the recombinant microorganism, the modified alcohol dehydrogenase sequence comprises an amino acid substitution at residue I173 with a V, T, A, L, F, or Y amino acid residue. In some embodiments of the recombinant microorganism, the modified alcohol dehydrogenase sequence comprises an amino acid substitution at residue I175 with a V or A amino acid residue. In some embodiments of the recombinant microorganism, the modified alcohol dehydrogenase sequence comprises an amino acid substitution at residue R200 with a R, G, S, or N amino acid residue. In some embodiments of the recombinant microorganism, the modified alcohol dehydrogenase sequence comprises an amino acid substitution at residue P201 with a P, E, D, K, or S amino acid residue. In some embodiments of the recombinant microorganism, the modified alcohol dehydrogenase sequence comprises an amino acid substitution at residue C203 with an R or K amino acid residue. In some embodiments of the recombinant microorganism, the modified alcohol dehydrogenase sequence comprises an amino acid substitution at residue G244 with an A, C, M, F, I, W, L, H, or P amino acid residue. In some embodiments of the recombinant microorganism, the modified alcohol dehydrogenase sequence comprises an amino acid substitution at residue E247 with a D, N, Q, or H amino acid residue. In some embodiments of the recombinant microorganism, the modified alcohol dehydrogenase sequence comprises an amino acid substitution at residue T248 with an S, N, A, L, M, or V amino acid residue.

In some embodiments of the recombinant microorganism, the modified alcohol dehydrogenase sequence comprises one or more of the following amino acid substitutions: G198E, E247Q, E247D, E247N, Y218F, G198D, I173C, G198L, S199D, Y218P, or Y218A.

In some embodiments of the recombinant microorganism, the modified alcohol dehydrogenase sequence comprises G198E and E247Q amino acid substitutions. In some embodiments of the recombinant microorganism, the modified alcohol dehydrogenase sequence comprises a G198E amino acid substitution. In some embodiments of the recombinant microorganism, the modified alcohol dehydrogenase sequence comprises G198E and Y218F amino acid substitutions. In some embodiments of the recombinant microorganism, the modified alcohol dehydrogenase sequence comprises G198E and E247D amino acid substitutions. In some embodiments of the recombinant microorganism, the modified alcohol dehydrogenase sequence comprises G198E and E247N amino acid substitutions. In some embodiments of the recombinant microorganism, the modified alcohol dehydrogenase sequence comprises G198D and Y218F amino acid substitutions. In some embodiments of the recombinant microorganism, the modified alcohol dehydrogenase sequence comprises I173C and G198E amino acid substitutions. In some embodiments of the recombinant microorganism, the modified alcohol dehydrogenase sequence comprises a G198D amino acid substitution. In some embodiments of the recombinant microorganism, the modified alcohol dehydrogenase sequence comprises G198L and S199D amino acid substitutions. In some embodiments of the recombinant microorganism, the modified alcohol dehydrogenase sequence comprises G198D and Y218P amino acid substitutions. In some embodiments of the recombinant microorganism, the modified alcohol dehydrogenase sequence comprises G198E and Y218P amino acid substitutions. In some embodiments of the recombinant microorganism, the modified alcohol dehydrogenase sequence comprises G198D and Y218A amino acid substitutions.

In some embodiments of the recombinant microorganism, the modified alcohol dehydrogenase is NADH-dependent In some embodiments, the modified alcohol dehydrogenase may comprise any one or more mutations described in FIG. 1. In some embodiments, the recombinant microorganism may express any one or more polypeptides comprising any one or more of the mutations described in FIG. 1. In some embodiments. The nucleic acid construction may encode a polypeptide sequence comprising any one or more of the mutations described in FIG. 1.

In some embodiments, the modified alcohol dehydrogenase may comprise any one or more mutations described in FIG. 2. In some embodiments, the recombinant microorganism may express any one or more polypeptides comprising any one or more of the mutations described in FIG. 2. In some embodiments. The nucleic acid construction may encode a polypeptide sequence comprising any one or more of the mutations described in FIG. 2.

In some embodiments, the modified alcohol dehydrogenase may comprise any one or more mutations described in FIG. 3. In some embodiments, the recombinant microorganism may express any one or more polypeptides comprising any one or more of the mutations described in FIG. 3. In some embodiments. The nucleic acid construction may encode a polypeptide sequence comprising any one or more of the mutations described in FIG. 3.

In some embodiments, the modified alcohol dehydrogenase may comprise any one or more mutations described in FIG. 4. In some embodiments, the recombinant microorganism may express any one or more polypeptides comprising any one or more of the mutations described in FIG. 4. In some embodiments. The nucleic acid construction may encode a polypeptide sequence comprising any one or more of the mutations described in FIG. 4.

In some embodiments, the modified alcohol dehydrogenase may comprise any one or more mutations described in FIG. 5. In some embodiments, the recombinant microorganism may express any one or more polypeptides comprising any one or more of the mutations described in FIG. 5. In some embodiments. The nucleic acid construction may encode a polypeptide sequence comprising any one or more of the mutations described in FIG. 5.

In some embodiments, the modified alcohol dehydrogenase may comprise any one or more mutations described in FIG. 6. In some embodiments, the recombinant microorganism may express any one or more polypeptides comprising any one or more of the mutations described in FIG. 6. In some embodiments. The nucleic acid construction may encode a polypeptide sequence comprising any one or more of the mutations described in FIG. 6.

In some embodiments, the modified alcohol dehydrogenase may comprise any one or more mutations described in FIG. 7. In some embodiments, the recombinant microorganism may express any one or more polypeptides comprising any one or more of the mutations described in FIG. 7. In some embodiments. The nucleic acid construction may encode a polypeptide sequence comprising any one or more of the mutations described in FIG. 7.

In some embodiments, the modified alcohol dehydrogenase may comprise any one or more mutations described in FIG. 8. In some embodiments, the recombinant microorganism may express any one or more polypeptides comprising any one or more of the mutations described in FIG. 8. In some embodiments. The nucleic acid construction may encode a polypeptide sequence comprising any one or more of the mutations described in FIG. 8.

BRIEF DESCRIPTION OF THE DRAWINGS

Aspects of the disclosure are illustrated in the drawings, in which:

FIG. 1 illustrates a tabulation of enzyme kinetics for the use of NADH or Acetone in an assay for alcohol dehydrogenase (ADH) activity in a modified (G198D, S199V, P201E, and Y218A) ADH from each of *Clostridium beijerinckii* and *Clostridium autoethanogenum*.

FIG. 2 illustrates a tabulation of enzyme kinetics for the use of NADPH or Acetone in an assay for alcohol dehydrogenase (ADH) activity in a modified (G198D, S199V, P201E, and Y218A) ADH from each of *Clostridium beijerinckii* and *Clostridium autoethanogenum*.

FIG. 3 illustrates a tabulation of enzyme kinetics for the use of NADH or Acetone in an assay for alcohol dehydrogenase (ADH) activity in multiple modified ADHs from *Clostridium beijerinckii*.

FIG. 4 illustrates a tabulation of enzyme kinetics for the use of NADPH or Acetone in an assay for alcohol dehydrogenase (ADH) activity in multiple modified ADHs from *Clostridium beijerinckii*.

FIG. 5 illustrates a tabulation of *Clostridium beijerinckii* alcohol dehydrogenase (ADH) mutants with an affirmative or negative indication as to whether the mutants accept NADH or NADPH cofactors.

FIG. 6 illustrates a tabulation of *Clostridium beijerinckii* alcohol dehydrogenase (ADH) mutants that were tested for NADH or NADPH cofactor acceptance.

FIG. 7 illustrates a tabulation of the amino acid residues of *Clostridium beijerinckii* alcohol dehydrogenase (ADH) which may be mutated to cause a switch in preferential usage of NADH to NADPH as a cofactor, and in some aspects the residues which may be utilized.

FIG. 8 depicts a list of positive tested mutants for NADH acceptance.

FIG. 10 illustrates a depiction of the tabulation of *Clostridium beijerinckii* alcohol dehydrogenase (ADH) alignment with possible mutations based on alignments of ADH with the NADH motif.

DETAILED DESCRIPTION

Definitions

Figure 9:
FIG. 9 illustrates a depiction of the tabulation of *Clostridium beijerinckii* alcohol dehydrogenase (ADH) alignment with possible mutations based on alignments of ADH with the NADPH motif.

The following definitions and abbreviations are to be used for the interpretation of the disclosure.

As used herein and in the appended claims, the singular forms "a," "an," and "the" include plural referents unless the context clearly dictates otherwise. Thus, for example, reference to "a three-carbon compound" includes a plurality of such three-carbon compounds and reference to "the microorganism" includes reference to one or more microorganisms, and so forth.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukaryota, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganisms. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus,*

*Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotide oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The terms nucleic acid "constructs" or "vectors" and like terms should be taken broadly to include any nucleic acid (including DNA, cDNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector Nucleic acid constructs or vectors include naked nucleic acids as well as nucleic acids formulated with one or more agents to facilitate delivery to a cell (for example, liposome-conjugated nucleic acid, an organism in which the nucleic acid is contained). The vectors may be used for cloning or expression of nucleic acids and for transformation of microorganisms to produce recombinant microorganisms. The vectors may include one or more nucleic acids encoding one or more alcohol dehydrogenase enzyme of the disclosure.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) Molecular Cloning: A Laboratory Manual (2nd ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different cell types, or at different stages of development, or in response to different environmental conditions. It is further recognized that since in most cases the exact boundaries of regulatory sequences have not been completely defined, DNA fragments of some variation may have identical promoter activity.

As used herein, a "constitutive promoter" is a promoter which is active under most conditions and/or during most development stages. There are several advantages to using constitutive promoters in expression vectors used in biotechnology, such as: high level of production of proteins used to select transgenic cells or organisms; high level of expression of reporter proteins or scoreable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

As used herein, the term "non-naturally occurring," when used in reference to a microorganism, organism, or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above. As used herein, the term "operably linked" refers to the association of nucleic acid sequences on a single nucleic acid fragment so that the function of one is regulated by the other.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. These variants may be referred to herein as "functionally equivalent variants" A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the enzyme.

The alcohol dehydrogenase enzymes of the disclosure are referred to herein to have "increased specificity" for one substrate over another. This is intended to mean that the alcohol dehydrogenase has increased specificity for one substrate relative to another, compared to the wild type alcohol dehydrogenase. It should not be taken to necessarily infer that an alcohol dehydrogenase of the disclosure has a higher specificity for a particular substrate compared to the wild type alcohol dehydrogenase, although this may be the case in some embodiments. Additionally, the term should not be taken to mean that an alcohol dehydrogenase of the disclosure has absolute specificity for a particular substrate over another, although this may be the case in some embodiments, and includes at least a preference for a particular substrate over another substrate.

"Increased specificity", "higher specificity", "preferential specificity" or like terms, when used in relation to an NADH or NADPH co-factor, refers to the degree of affinity with which a co-factor binds to an alcohol dehydrogenase during a reaction. It should not be taken to mean that an alcohol dehydrogenase and a co-factor have absolute specificity, although this may be the case, and includes at least a preference for the binding between a particular alcohol dehydrogenase and one co-factor over another co-factor.

As used herein, the term "cofactor specificity" or "cofactor preference" is a measure of the specificity of an enzyme for one cofactor over another. Thus the methods of the present invention may be used to alter the cofactor preference of the target enzyme, such that the preference for the less favored cofactor is increased by 1%, 2%, 3%, 4%, 5%, 6%, 7%, 8%, 90%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99, 100%, 125%, 150%, 175%, 200%, 250%, 300%, 350%, 400%, 450%, 500%, 600%, 700%, 800%, 900%, 1,000%, 2,000%, 3,000%, 4,000%, 5,000%. For target proteins that prefer NADPH as a cofactor, it would be desirable to alter the cofactor specificity of the target enzyme (e.g., an alcohol dehydrogenase) to a cofactor that is more readily available, such as NADH.

Alcohol Dehydrogenase (ADH)

The disclosure identifies modifications of alcohol dehydrogenase that result in an increased or preferential specificity for one or more substrates and/or cofactors over other substrates and/or cofactors. This disclosure contemplates that the modification and use of a wide variety of alcohol dehydrogenases from a wide variety of organisms, including alcohol dehydrogenases that exhibit activity towards primary and/or secondary alcohols, and uses NADH and/or NADPH as substrate/cofactor (EC 1.1.1.1 or EC 1.1.1.2). In one embodiment, the wt alcohol dehydrogenase is selected from any one of the microorganisms set forth in the present disclosure.

The ADH from wt strains C. beijerinckii are known to exhibit enzymatic activity on acetone and butyraldehyde in the presence of cofactor NADPH; however, the strains exhibited no measurable enzymatic activity on acetone and butyraldehyde in the presence of cofactor NADH. See Ismaiel et al. (1993. J. Bac. 175(16):5097-5105).

In some embodiments, alcohol dehydrogenases of the present disclosure share at least 50%, at least 55%, at least 60%, at least 65%, at least 70%, at least 75%, at least 80%, at least 85%, at least 90%, at least 95%, at least 99%, or at least 100% sequence identity with SEQ ID NO:2.

In some embodiments, alcohol dehydrogenases of the present disclosure share at least about 50%, at least about 55%, at least about 60%, at least about 65%, at least about 70%, at least about 75%, at least about 80%, at least about 85%, at least about 90%, at least 9 about 5%, at least about 99%, or at least about 100% sequence identity with SEQ ID NO:2.

In some embodiments, alcohol dehydrogenases of the present disclosure are encoded by polynucleotide sequences that share at least 50%, at least 55%, at least 60%, at least 65%, at least 70%, at least 75%, at least 80%, at least 85%, at least 90%, at least 95%, at least 99%, or at least 100% sequence identity with SEQ ID NO:1.

In some embodiments, alcohol dehydrogenases of the present disclosure are encoded by polynucleotide sequences that share at least about 50%, at least about 55%, at least about 60%, at least about 65%, at least about 70%, at least about 75%, at least about 80%, at least about 85%, at least about 90%, at least 9 about 5%, at least about 99%, or at least about 100% sequence identity with SEQ ID NO:1.

In some embodiments, alcohol dehydrogenases of the present disclosure comprise at least one mutation/modification compared to the corresponding wt alcohol dehydrogenase.

In some embodiments, the modified alcohol dehydrogenase comprises an amino acid substitution at one or more of the following residues: T38, G198, S199, Y218, I175, I173, R200, P201, C203, G244, E247, T248, K219, G243, Q251, Y267, L294, C295, K340, and K342.

In some embodiments, the modified alcohol dehydrogenase comprises an amino acid substitution at T38 with an H amino acid residue.

In some embodiments, the modified alcohol dehydrogenase comprises an amino acid substitution at residue G198 with a D, E, G, K, N, R, S, A, or V amino acid residue.

In some embodiments, the modified alcohol dehydrogenase comprises an amino acid substitution at residue S199 with a D, G, H, I, L, N, R, S, V, C, M, or P amino acid residue.

In some embodiments, the modified alcohol dehydrogenase comprises an amino acid substitution at residue Y218 with a P, A, D, F, I, N, S, T, V, Y, H, L, or Y amino acid residue.

In some embodiments, the modified alcohol dehydrogenase comprises an amino acid substitution at residue I173 with a V, T, A, L, T, F, or Y amino acid residue.

In some embodiments, the modified alcohol dehydrogenase comprises an amino acid substitution at residue I175 with a V or A amino acid residue.

In some embodiments, the modified alcohol dehydrogenase comprises an amino acid substitution at residue R200 with a R, G, S, or N amino acid residue.

In some embodiments, the modified alcohol dehydrogenase comprises an amino acid substitution at residue P201 with a P, E, D, K, or S amino acid residue.

In some embodiments, the modified alcohol dehydrogenase comprises an amino acid substitution at residue C203 with an R or K amino acid residue.

In some embodiments, the modified alcohol dehydrogenase comprises an amino acid substitution at residue G244 with an A, C, M, F, I, W, L, H, or P amino acid residue.

In some embodiments, the modified alcohol dehydrogenase comprises an amino acid substitution at residue E247 with a D, N, Q, or H amino acid residue.

In some embodiments, the modified alcohol dehydrogenase comprises an amino acid substitution at residue T248 with an S, N, A, L, M, or V amino acid residue.

In some embodiments, the modified alcohol dehydrogenase comprises one or more of the following amino acid substitutions: I173C, G198E, G218F, Y218P, Y218A, Y218W, S199D, S199L, G244A, G244L, G244C, E247D, E247N, E247Q, G198D, S199G, S199V, P201E, P201R, I175R, and Y218D.

In some embodiments, the modified alcohol dehydrogenase comprises amino acid substitution G198E and only one additional substitution selected from the following amino acid substitutions: I173C, G218F, Y218P, Y218A, Y218W, S199D, S199L, G244A, G244L, G244C, E247D, E247N, E247Q, G198D, S199G, S199V, P201E, P201R, I175R, and Y218D.

In some embodiments, the modified alcohol dehydrogenase comprises amino acid substitution G198E and at least one additional substitution selected from the following amino acid substitutions: I173C, G218F, Y218P, Y218A, Y218W, S199D, S199L, G244A, G244L, G244C, E247D, E247N, E247Q, G198D, S199G, S199V, P201E, P201R, I175R, and Y218D.

In some embodiments, the modified alcohol dehydrogenase comprises fewer than 4 amino acid substitutions. In some embodiments, the modified alcohol dehydrogenase comprises fewer than 3 amino acid substitutions. In some embodiments, the modified alcohol dehydrogenase comprises 2 amino acid substitutions. In some embodiments, the modified alcohol dehydrogenase comprises 3 amino acid substitutions. In some embodiments, the modified alcohol dehydrogenase comprises 4 amino acid substitutions. In some embodiments, the modified alcohol dehydrogenase comprises at least 1 amino acid substitution. In some embodiments, the modified alcohol dehydrogenase comprises at least 2 amino acid substitutions. In some embodiments, the modified alcohol dehydrogenase comprises at least 3 amino acid substitutions. In some embodiments, the modified alcohol dehydrogenase comprises at least 4 amino acid substitutions.

In some embodiments, the modified alcohol dehydrogenase comprises a G198E amino acid substitution. In some embodiments, the modified alcohol dehydrogenase comprises a G198D amino acid substitution. In some embodiments, the modified alcohol dehydrogenase comprises an amino acid substitution at G198E and I173C. In some embodiments, the modified alcohol dehydrogenase comprises an amino acid substitution at G198E and Y218F. In some embodiments, the modified alcohol dehydrogenase comprises an amino acid substitution at G198E and Y218P. In some embodiments, the modified alcohol dehydrogenase comprises an amino acid substitution at G198E and Y218A. In some embodiments, the modified alcohol dehydrogenase comprises an amino acid substitution at G198E and Y218W. In some embodiments, the modified alcohol dehydrogenase comprises an amino acid substitution at G198E and S199D. In some embodiments, the modified alcohol dehydrogenase comprises an amino acid substitution at G198E and S199I. In some embodiments, the modified alcohol dehydrogenase comprises an amino acid substitution at G198E and G244A. In some embodiments, the modified alcohol dehydrogenase comprises an amino acid substitution at G198E and G244L. In some embodiments, the modified alcohol dehydrogenase comprises an amino acid substitution at G198E and G244C. In some embodiments, the modified alcohol dehydrogenase comprises an amino acid substitution at G198E and E247D. In some embodiments, the modified alcohol dehydrogenase comprises an amino acid substitution at G198E and E247N. In some embodiments, the modified alcohol dehydrogenase comprises an amino acid substitution at G198E and E247Q. In some embodiments, the modified alcohol dehydrogenase comprises an amino acid substitution at G198D and S199I. In some embodiments, the modified alcohol dehydrogenase comprises an amino acid substitution at G198D and S199G. In some embodiments, the modified alcohol dehydrogenase comprises an amino acid substitution at G198D and Y218F. In some embodiments, the modified alcohol dehydrogenase comprises an amino acid substitution at G198D and Y218P. In some embodiments, the modified alcohol dehydrogenase comprises an amino acid substitution at G198D and Y218W. In some embodiments, the modified alcohol dehydrogenase comprises an amino acid substitution at G198D and Y218A. In some embodiments, the modified alcohol dehydrogenase comprises an amino acid substitution at G198D, S199V, P201E, and Y218A. In some embodiments, the modified alcohol dehydrogenase comprises an amino acid substitution at G198D S199V, and P201R. In some embodiments, the modified alcohol dehydrogenase comprises an amino acid substitution at G198L and S199D. In some embodiments, the modified alcohol dehydrogenase comprises an amino acid substitution at I175R, G198L, S199D, and Y218D.

In some embodiments, the amino acid substitutions of the present disclosure are relative to SEQ ID NO:2. In some embodiments, the amino acid substitutions of the present disclosure are relative to wt alcohol dehydrogenases. In some embodiments, the amino acid substitutions of the present disclosure are relative to wt microbial alcohol dehydrogenases. In some embodiments, the amino acid substitutions of the present disclosure are relative to wt bacterial alcohol dehydrogenases.

In some embodiments, the modified alcohol dehydrogenase exhibits an increased specificity for NADH over NADPH as a cofactor, exhibits the ability to utilize NADH as a cofactor, or exhibits NADH dependence as a cofactor.

In some embodiments, the modified alcohol dehydrogenase exhibits an increased specificity for NADH over NADPH, as compared to a corresponding unmodified alcohol dehydrogenase. In some embodiments, the modified alcohol dehydrogenase exhibits an increased specificity for NADH over NADPH by at least 5%, at least 10%, at least 15%, at least 20%, at least 25%, at least 30%, at least 35%, at least 40%, at least 45%, at least 50%, at least 55%, at least 60%, at least 75%, at least 80%, at least 85%, at least 90%, at least 95%, at last 100%, at least 200%, at least 300%, at least 400%, at least 500%, at least 600%, at least 700%, at least 800%, at least 900%, or at least 1,000% as compared to a corresponding unmodified alcohol dehydrogenase.

In some embodiments, the modified alcohol dehydrogenase exhibits an increased specificity for NADH over NADPH by at least about 5%, at least about 10%, at least about 15%, at least about 20%, at least about 25%, at least about 30%, at least about 35%, at least about 40%, at least about 45%, at least about 50%, at least about 55%, at least about 60%, at least about 75%, at least about 80%, at least about 85%, at least about 90%, at least about 95%, at last about 100%, at least about 200%, at least about 300%, at least about 400%, at least about 500%, at least about 600%, at least about 700%, at least about 800%, at least about 900%, or at least about 1,000% as compared to a corresponding unmodified alcohol dehydrogenase.

In some embodiments, the modified alcohol dehydrogenase exhibits an increased specificity for NADH over NADPH at a ratio of 1:10, 2:10, 3:10, 4:10, 5:10, 6:10, 7:10, 8:10, 9:10, 1:1, 2:1, 3:1, 4:1, 5:1, 6:1, 7:1, 8:1, 9:1, 10:1, 15:1, 20:1, 25:1, 30:1, 35:1, 40:1, 45:1, 50:1, 100:1, 200:1, 300:1, 400:1, 500:1, 600:1, 700:1, 800:1, 900:1, or 1,000:1.

In some embodiments, the modified alcohol dehydrogenase exhibits an increased specificity for NADH over NADPH at a ratio of at least 1:10, at least 2:10, at least 3:10, at least 4:10, at least 5:10, at least 6:10, at least 7:10, at least 8:10, at least 9:10, at least 1:1, at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 100:1, at least 200:1, at least 300:1, at least 400:1, at least 500:1, at least 600:1, at least 700:1, at least 800:1, at least 900:1, or at least 1,000:1.

In some embodiments, the modified alcohol dehydrogenase exhibits an increased specificity for NADH over NADPH at a ratio of at least about 1:10, at least about 2:10, at least about 3:10, at least about 4:10, at least about 5:10, at least about 6:10, at least about 7:10, at least about 8:10, at least about 9:10, at least about 1:1, at least about 2:1, at least about 3:1, at least about 4:1, at least about 5:1, at least about 6:1, at least about 7:1, at least about 8:1, at least about 9:1, at least about 10:1, at least about 15:1, at least about 20:1, at least about 25:1, at least about 30:1, at least about 35:1, at least about 40:1, at least about 45:1, at least about 50:1, at least about 100:1, at least about 200:1, at least about 300:1, at least about 400:1, at least about 500:1, at least about 600:1, at least about 700:1, at least about 800:1, at least about 900:1, or at least about 1,000:1.

In some embodiments, the modified alcohol dehydrogenase utilizes both NADH and NADPH as a cofactor/substrate. In some embodiments, the modified alcohol dehydrogenase is a microbial alcohol dehydrogenase. In some embodiments, the modified alcohol dehydrogenase is a bacterial alcohol dehydrogenase. In some embodiments, the modified alcohol dehydrogenase is an Archaea alcohol dehydrogenase. In some embodiments, the modified alcohol dehydrogenase is a fungal alcohol dehydrogenase.

Nucleic Acids

The present disclosure relates to novel alcohol dehydrogenases, it further relates to nucleic acids encoding the alcohol dehydrogenases and nucleic acid constructs and vectors comprising the nucleic acids.

The present disclosure contemplates codon optimization of nucleic acids encoding an alcohol dehydrogenase of the disclosure, for any type of organisms.

In some embodiments, the disclosure contemplates nucleic acid vectors and/or constructs comprising one or more nucleic acids encoding one or more alcohol dehydrogenase of the disclosure. In some embodiments, nucleic acids of the disclosure may remain extrachromosomal upon transformation of a microorganism or may be adapted for integration into the genome of the microorganism. Accordingly, nucleic acids of the disclosure may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In some embodiments, nucleic acids encoding one or more alcohol dehydrogenase of the disclosure will comprise a promoter adapted to promote expression of the one or more enzymes encoded by the nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or an arabinose inducible pBAD promoter. It will be appreciated by those of skill in the art that other promoters which can direct expression, preferably a high level of expression under appropriate fermentation conditions, would be effective as alternatives to the exemplified embodiments.

In some embodiments, nucleic acids and nucleic acid constructs, including expression constructs/vectors of the disclosure may be constructed using any number of techniques standard in the art. For example, chemical synthesis, site directed mutagenesis, or recombinant techniques may be used. Such techniques are described, for example, in Sambrook et al (Molecular Cloning: A laboratory manual, Cold Spring Harbor Laboratory Press, Cold Spring Harbor, NY, 1989) Suitable vectors for use in the disclosure will be appreciated by those of ordinary skill in the art.

Microorganisms

The microorganisms of the disclosure may be prepared from a parental microorganism using any number of techniques known in the art, including, for example, site directed mutagenesis techniques to introduce the desired mutation(s) into an alcohol dehydrogenase gene native to a parental microorganism, or other recombinant technologies to introduce one or more nucleic acid encoding one or more alcohol dehydrogenase of the disclosure into a parental microorganism.

In one embodiment, one or more exogenous nucleic acid encoding one or more alcohol dehydrogenase is introduced into a parental microorganism and replaces one or more alcohol dehydrogenase gene native to the parental microorganism. In another embodiment, one or more exogenous nucleic acid encoding one or more alcohol dehydrogenase of the disclosure is introduced to a parental microorganism and is supplementary to an alcohol dehydrogenase gene native to the parental microorganism. In other embodiments, one or more exogenous nucleic acid is introduced into a parental microorganism to introduce one or more desired mutation into one or more alcohol dehydrogenase gene native to the parental microorganism. In another embodiment, one or more exogenous nucleic acid encoding one or more alcohol dehydrogenase is introduced into a parental microorganism, and one or more mutation is introduced to one or more alcohol dehydrogenase gene native to the parental microorganism to reduce or knock out its expression and activity.

In one embodiment, a microorganism of the disclosure is prepared from a parental microorganism using recombinant technology. For example, a parental microorganism is transformed with one or more exogenous nucleic acid encoding an alcohol dehydrogenase of the disclosure, or one or more nucleic acid adapted to introduce a desired mutation to a native alcohol dehydrogenase gene in the parental microorganism. An exogenous nucleic acid may remain extrachromosomal upon transformation of the parent microorganism or may integrate into the genome of the parent microorganism (in one embodiment to replace a native alcohol dehydrogenase gene, or introduce a mutation into a native alcohol dehydrogenase gene). Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences), as described herein.

In one embodiment, transformation (including transduction or transfection) of a microorganism may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In one embodiment, one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) Microbial. Molec. Biol. Rev. 64, 412.)

In one embodiment, the recombinant microorganism is chosen from a group of microorganisms comprising bacteria, Archaea, and fungi.

In one embodiment, the recombinant microorganism is chosen from the genera *Clostridium, Acetobacterium, Moorella, Butyribacterium, Blautia, Oxobacter, Thermoanaerobacter, Escherichia, Klebsiella, Zymomonas, Citrobacter, Enterobacter, Salmonella, Serratia, Lactobacillus. Lactococcus. Enterococcus, Pediococcus, Streptococcus, Saccharomyces, Pichia, Candida hansemila, Yarrowia, Rhodotorula, Rhizopus, Trichosporon, Lipomyces, Aspergillus, trichoderma, Exophila, Mucor, Cladosporium, Phanerochaete, Cladophialophora, Paecilomyces, Scedosporium, Ophistoma, Bacillus, Oligotropha, Pseudomonas, Carbophilus, Hydrogenophaga, Mycobacterium, Zavarzinia, Cupravidus, Senechocystis, Chloroflexus, Methylomonas,*

*Methylobacter, Methylococcus, Methylomicrobium, Methylosphera, Methylocaldum, Methylocystis, Methylosinus, Methanobacterium, Methanococcus, Methanogenium, Methanosarcina, Methanosphaera, Methanothermobacter, Methanotrix, Corynebacterium, Acinetobacter, Actinomyces, Bacteroides, Burkholderia, Brevibacterium, Pyrococcus, Geobacter, Geobacillus, Paenibacillus, Mycobacterium, Rhodopseudomonas, Thermatoga, Thermoanaerobacter, Streptomyces, Rhodobacter, Rhodococcus, Peptococcus, Bifidobacterium, Propionibacterium, Fusobacterium, Campylobacter, Veillonella, Aquincola, Arthrobacter, Moraxella,* and *Psychrobacter.*

In one embodiment the organism is chosen from the group of carboxydotrophic acetogenic microorganisms, the group of Enterobacteria, the group of *Lactobacillus*, the group of fungi and yeasts, the group of aerobic carboxydotrophes, the group of aerobic $CO_2$ fixing organisms, the group of methylotrophes, and the group of methanogens.

In one embodiment, the microorganism is a carboxydotrophic acetogen selected from the group comprising *Clostridium autoethanogenum, Clostridium ljungdahlii, Clostridium ragsdalei, Clostridium carboxidivorans, Clostridium drakei, Clostridium scatologenes, Clostridium coskatii, Clostridium aceticum, Clostridium magnum, Clostridium* sp., *Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacier pfennigii,* and *Thermoanaerobacter kiuvi.* In one embodiment the microorganism is *Clostridium autoethanogenum,* or *Clostridium ljungdahlii.*

In one embodiment, the microorganism is a microorganism selected from the group comprising *Clostridium acetobutylicum, Clostridium beijerinckii, Clostridium saccharobutylicum, Clostridium saccharaoperbutylacetonicum.* In one embodiment the microorganism is *Clostridium acetobutylicum,* or *Clostridium beijerinckii.*

In one embodiment, the microorganism is an Enterobacteria selected from the group comprising *Escherichia, Klebsiella, Zymomonas, Citrobacter, Enterobacter, Salmonella,* and *Serratia.* In one embodiment the microorganism is *Escherichia coli, Zymomonas mobilis, Klebsiella pneumonia, Klebsiella oxtoca, Enterobacter cloacae,* or *Serrata marcescens.*

In one embodiment, the microorganism is a *Lactobacillus* selected from the group comprising *Lactobacillus, Lactococcus, Enterococcus, Pediococcus,* and *Streptococcus.* In one embodiment the microorganism is *Lactobacillus brevis, Enterococcus faecalis,* or *Lactococcus lactis.*

In one embodiment, the microorganism is a fungi or yeast selected from the group comprising *Saccharomyces. Pichia, Candida hansemila, Yarrowia, Rhodotorula, Rhizopus, Trichosporon, Lipomyces* and from the group comprising *Aspergillus, Trichoderma, Exophila, Mucor, Cladosporium, Phanerochaete, Cladophialophora, Paecilomyces, Scedosporium, Ophistoma.* In one embodiment the microorganism is Saccharomyces cerevisae. *Candida tropicalis, Candida albicans* or *Yarrowia lipolytica.* In one embodiment the microorganism is *Aspergillus niger,* or *Trichoderma reesei.*

In one embodiment, the microorganism is an aerobic carboxydotroph selected from the group comprising *Bacillus, Oligotropha, Pseudomonas, Carbophilus, Hydrogenophaga, Mycobacterium,* and *Zavarzinia.* In one embodiment the microorganism is *Oligotropha carboxidovorans, Carbophilus carboxidus, Hydrogenophaga pseudoflava, Mycobacterium* sp., *Pseudomonas carboxydohydrogena, Pseudomonas* sp., *Zavarzinia compransoris* or *Bacillus schlegelli.* In one embodiment, the microorganism is an aerobic $CO_2$ fixing organism selected from the group comprising *Cupravidus, Senechocystis,* and *Chloroflexus.* In one embodiment the microorganism is *Cupravidus necator, Synechocystis* sp., or *Chloroflexus aurantiacus.*

In one embodiment, the microorganism is a methylotroph selected from the group comprising *Methylomonas, Methylobacter, Methylococcus, Methylomicrobium, Methylosphera, Methylocaldum, Methylocystis,* or *Methylosinus.* In one embodiment the microorganism is *Methylococcus capsulatus,* or *Methylosinus trichosporium.*

In one embodiment, the microorganism is a methanogen selected from the group comprising *Methanobacterium, Methanococcus, Methanogenium, Methanosarcina, Methanosphaera, Methanothermobacter,* and *Methanotrix.* In one embodiment the microorganism is *Methanothermobacter marburgensis,* or Methanosarcina barkeri.

The present disclosure provides a method for producing isopropanol and/or acetone by microbial fermentation of a substrate using a recombinant microorganisms of the disclosure. In some embodiments, the isopropanol and/or acetone are collected or isolated. In some embodiments, the isopropanol and/or acetone are purified.

Example 1: Modification of Two Alcohol Dehydrogenases from *Clostridium*

Previous work indicated a cofactor preference change for NADH over NADPH in *Clostridium autoethanogenum* with G198D, S199V, P201E, and Y218A (DVEA mutant) mutations in the *C. autoethanogenum* alcohol dehydrogenase. (See PCT Publication No. WO2013152236A1, and Protein Engineering, Design & Selection. 2015. 28.8:251-258). The alcohol dehydrogenase from *Clostridium beijerinckii* shares 86% identity and 94% similarity to *C. autoethanogenum*. The *C. autoethanogenum* DVEA mutant of alcohol dehydrogenase was found to convert acetone to isopropanol utilizing NADH and/or NADPH.

The DVEA mutant was recreated in the alcohol dehydrogenase from *C. beijerinckii*, and compared against the DVEA mutant from *C. autoethanogenum* for NADH utilization (FIG. 1) and NADPH utilization (FIG. 2). The DVEA mutant from *C. beijerinckii* exhibited a significantly decreased catalytic efficiency for at least the NADH, as compared with the significantly higher catalytic efficiency exhibited by the DVEA mutant from *C. autoethanogenum*.

Example 2: Modifications of Alcohol Dehydrogenases from *Clostridium beijerinckii*

The *C. beijerinckii* alcohol dehydrogenase was utilized to make numerous mutations that resulted in between 1 and 4 amino acid substitutions in each of the alcohol dehydrogenase mutants (FIG. 6). FIG. 5 indicates the cofactor acceptance status for each of the tested mutants, indicating whether NADH and/or NADPH activity was present. FIG. 8 indicates the mutants that were capable of utilizing NADH, and FIG. 3 and FIG. 4 reveal the enzyme kinetics data for NADH and NADPH acceptance for a subset of the mutants from FIG. 8. FIG. 7 indicates the residues in the alcohol dehydrogenase that are hot spots for substitutions that can confer NADH acceptance, with some of the possible mutations indicated for some of the residues. FIG. 9 and FIG. 10 indicate the alignment with possible mutations based upon alignments with the alcohol dehydrogenase and the NADH and NADPH motifs.

The previous work with alcohol dehydrogenase from *C. autoethanogenum* required several mutations (DVEA mutant; See PCT Publication No. WO2013152236A1). However, FIG. 3 demonstrates NADH cofactor acceptance in mutants that only required two amino acid substitutions in the alcohol dehydrogenase. Comparing the results of FIG. 3 (*C. beijerinckii*) with the *C. autoethanogenum* of FIG. 1 makes it abundantly clear that fewer substitutions in the alcohol dehydrogenases can be made to yield enzyme activity that surpasses that of the *C. autoethanogenum* DVEA mutant.

EMBODIMENTS OF THE DISCLOSURE

1. A nucleic acid construct comprising a polynucleotide sequence encoding a modified alcohol dehydrogenase, wherein the alcohol dehydrogenase exhibits activity with cofactor NADH as compared to an unmodified alcohol dehydrogenase; and wherein the polynucleotide sequence shares at least 85% sequence identity with SEQ ID NO:1.
2. A nucleic acid construct of embodiment 1, wherein the modified alcohol dehydrogenase exhibits a cofactor preference for NADH over NADPH, as compared to an unmodified alcohol dehydrogenase.
3. The nucleic acid construct of embodiment 1, wherein the modified alcohol dehydrogenase exhibits an increased activity for reduction of acetone to isopropanol with NADH, as compared to an unmodified alcohol dehydrogenase.
4. The nucleic acid construct of embodiment 1, wherein the modified alcohol dehydrogenase exhibits an increased activity for oxidation of isopropanol to acetone, as compared to an unmodified alcohol dehydrogenase.
5. The nucleic acid construct of embodiments 3 or 4, wherein the modified alcohol dehydrogenase exhibits at least a 10 fold increase in activity with cofactor NADH as compared to an unmodified alcohol dehydrogenase.
6. The nucleic acid construct of embodiment 1, wherein the polynucleotide shares at least 90% sequence identity with SEQ ID NO:1.
7. The nucleic acid construct of embodiment 1, wherein the polynucleotide shares at least 95% sequence identity with SEQ ID NO:1.
8. The nucleic acid construct of embodiment 1, wherein the polynucleotide shares at least 99% sequence identity with SEQ ID NO:1.
9. The nucleic acid construct of embodiment 1, wherein the modified alcohol dehydrogenase is a secondary alcohol dehydrogenase.
10. The nucleic acid construct of embodiment 1, wherein the modified alcohol dehydrogenase is NADH-dependent.
11. The nucleic acid construct of embodiment 1, wherein the modified alcohol dehydrogenase is a microbial alcohol dehydrogenase.
12. The nucleic acid construct of embodiment 11, wherein the microbial alcohol dehydrogenase is a bacterial alcohol dehydrogenase.
13. The nucleic acid construct of embodiment 12, wherein the bacterial alcohol dehydrogenase is a *Clostridium beijerinckii* alcohol dehydrogenase.
14. A polypeptide sequence comprising a modified alcohol dehydrogenase that exhibits activity with cofactor NADH as compared to an unmodified alcohol dehydrogenase; and wherein the modified alcohol dehydrogenase shares at least 85% sequence identity with SEQ ID NO:2.
15. The polypeptide sequence of embodiment 14, wherein the modified alcohol dehydrogenase exhibits a cofactor preference for NADH over NADPH, as compared to an unmodified alcohol dehydrogenase.
16. The polypeptide sequence of embodiment 14, wherein the modified alcohol dehydrogenase exhibits an increased activity for reduction of acetone to isopropanol with NADH, as compared to an unmodified alcohol dehydrogenase.
17. The polypeptide sequence of embodiment 14, wherein the modified alcohol dehydrogenase exhibits an increased activity for oxidation of isopropanol to acetone, as compared to an unmodified alcohol dehydrogenase.
18. The polypeptide sequence of embodiments 16 or 17, wherein the modified alcohol dehydrogenase exhibits at least a 10 fold increase in activity with cofactor NADH as compared to an unmodified alcohol dehydrogenase.
19. The polypeptide sequence of embodiment 14, wherein the modified alcohol dehydrogenase shares at least 90% sequence identity with SEQ ID NO:2.
20. The polypeptide sequence of embodiment 14, wherein the modified alcohol dehydrogenase shares at least 95% sequence identity with SEQ ID NO:2.
21. The polypeptide sequence of embodiment 14, wherein the modified alcohol dehydrogenase shares at least 99% sequence identity with SEQ ID NO:2.
22. The polypeptide sequence of embodiment 14, wherein the alcohol dehydrogenase is a secondary alcohol dehydrogenase.
23. The polypeptide sequence of embodiment 14, wherein the modified alcohol dehydrogenase is NADH-dependent.
24. The polypeptide sequence of embodiment 14, wherein the modified alcohol dehydrogenase is a microbial alcohol dehydrogenase.
25. The polypeptide sequence of embodiment 24, wherein the microbial alcohol dehydrogenase is a bacterial alcohol dehydrogenase.
26. The polypeptide sequence of embodiment 25, wherein the bacterial alcohol dehydrogenase is a *Clostridium beijerinckii* alcohol dehydrogenase.
27. The polypeptide sequence of embodiment 14, wherein the polypeptide sequence comprises a signal peptide.
28. The polypeptide sequence of embodiment 27, wherein the signal peptide is a secretion signal.
29. The polypeptide sequence of embodiment 14, wherein the modified alcohol dehydrogenase sequence is selected from SEQ ID NOs: 3-38.
30. The polypeptide sequence of embodiment 14, wherein the modified alcohol dehydrogenase sequence comprises an amino acid substitution at one or more of the following residues: T38, G198, S199, Y218, I175, I173, R200, P201, C203, G244, E247, T248, K219, G243, Q251, Y267, L294, C295, K340, and K342.
31. The polypeptide sequence of embodiment 14, wherein the modified alcohol dehydrogenase sequence comprises an amino acid substitution at residue T38 with an H amino acid residue.
32. The polypeptide sequence of embodiment 14, wherein the modified alcohol dehydrogenase sequence comprises an amino acid substitution at residue G198 with a D, E, G, K, N, R, S, A, or V amino acid residue.

33. The polypeptide sequence of embodiment 14, wherein the modified alcohol dehydrogenase sequence comprises an amino acid substitution at residue S199 with a D, G, H, I, L, N, R, S, V, C, M, or P amino acid residue.
34. The polypeptide sequence of embodiment 14, wherein the modified alcohol dehydrogenase sequence comprises an amino acid substitution at residue Y218 with a P, A, D, F, I, N, S, T, V, H, L, or Y amino acid residue.
35. The polypeptide sequence of embodiment 14, wherein the modified alcohol dehydrogenase sequence comprises an amino acid substitution at residue I173 with a V, T, A, L, F, or Y amino acid residue.
36. The polypeptide sequence of embodiment 14, wherein the modified alcohol dehydrogenase sequence comprises an amino acid substitution at residue I175 with a V or A amino acid residue.
37. The polypeptide sequence of embodiment 14, wherein the modified alcohol dehydrogenase sequence comprises an amino acid substitution at residue R200 with a R, G, S, or N amino acid residue.
38. The polypeptide sequence of embodiment 14, wherein the modified alcohol dehydrogenase sequence comprises an amino acid substitution at residue P201 with a P, E, D, K, or S amino acid residue.
39. The polypeptide sequence of embodiment 14, wherein the modified alcohol dehydrogenase sequence comprises an amino acid substitution at residue C203 with an R or K amino acid residue.
40. The polypeptide sequence of embodiment 14, wherein the modified alcohol dehydrogenase sequence comprises an amino acid substitution at residue G244 with an A, C, M, F, I, W, L, H, or P amino acid residue.
41. The polypeptide sequence of embodiment 14, wherein the modified alcohol dehydrogenase sequence comprises an amino acid substitution at residue E247 with a D, N, Q, or H amino acid residue.
42. The polypeptide sequence of embodiment 14, wherein the modified alcohol dehydrogenase sequence comprises an amino acid substitution at residue T248 with an S, N, A, L, M, or V amino acid residue.
43. The polypeptide sequence of embodiment 14, wherein the modified alcohol dehydrogenase sequence comprises one or more of the following amino acid substitutions: G198E, E247Q, E247D, E247N, Y218F, G198D, I173C, G198L, S199D, Y218P, or Y218A.
44. The polypeptide sequence of embodiment 14, wherein the modified alcohol dehydrogenase sequence comprises G198E and E247Q amino acid substitutions.
45. The polypeptide sequence of embodiment 14, wherein the modified alcohol dehydrogenase sequence comprises a G198E amino acid substitution.
46. The polypeptide sequence of embodiment 14, wherein the modified alcohol dehydrogenase sequence comprises G198E and Y218F amino acid substitutions.
47. The polypeptide sequence of embodiment 14, wherein the modified alcohol dehydrogenase sequence comprises G198E and E247D amino acid substitutions.
48. The polypeptide sequence of embodiment 14, wherein the modified alcohol dehydrogenase sequence comprises G198E and E247N amino acid substitutions.
49. The polypeptide sequence of embodiment 14, wherein the modified alcohol dehydrogenase sequence comprises G198D and Y218F amino acid substitutions.
50. The polypeptide sequence of embodiment 14, wherein the modified alcohol dehydrogenase sequence comprises I173C and G198E amino acid substitutions.
51. The polypeptide sequence of embodiment 14, wherein the modified alcohol dehydrogenase sequence comprises a G198D amino acid substitution.
52. The polypeptide sequence of embodiment 14, wherein the modified alcohol dehydrogenase sequence comprises G198L and S199D amino acid substitutions.
53. The polypeptide sequence of embodiment 14, wherein the modified alcohol dehydrogenase sequence comprises G198D and Y218P amino acid substitutions.
54. The polypeptide sequence of embodiment 14, wherein the modified alcohol dehydrogenase sequence comprises G198E and Y218P amino acid substitutions.
55. The polypeptide sequence of embodiment 14, wherein the modified alcohol dehydrogenase sequence comprises G198D and Y218A amino acid substitutions.
56. The polypeptide sequence of embodiment 14, wherein the modified alcohol dehydrogenase is NADH-dependent.
57. A recombinant microorganism comprising the nucleic acid construct of any one of embodiment 1-13.
58. A method of producing a recombinant microorganism that produces a modified alcohol dehydrogenase that exhibits activity with cofactor NADH as compared to an unmodified alcohol dehydrogenase, the method comprising introducing a polynucleotide sequence encoding the polypeptide sequence of any one of embodiments 14-56 into a microorganism.
59. The method of embodiment 58, wherein the microorganism is a bacterium.
60 The method of embodiment 59, wherein the bacterium is a species of *Escherichia* or *Bacillus*.
61. The method of embodiment 60, wherein the bacterium is *Escherichia coli*.
62. The method of embodiment 58, wherein the microorganism is a fungus.
63. The method of embodiment 62, wherein the fungus is a yeast.
64. The method of embodiment 62, wherein the fungus is a species of *Saccharomyces, Pichia* or *Aspergillus*.
65. The method of embodiment 58, wherein the modified alcohol dehydrogenase exhibits a cofactor preference for NADH over NADPH, as compared to an unmodified alcohol dehydrogenase.
66. A recombinant microorganism expressing a polypeptide sequence comprising a modified alcohol dehydrogenase that exhibits activity with cofactor NADH as compared to an unmodified alcohol dehydrogenase; and wherein the modified alcohol dehydrogenase shares at least 85% sequence identity with SEQ ID NO:2.
67. The recombinant microorganism of embodiment 66, wherein the modified alcohol dehydrogenase exhibits a cofactor preference for NADH over NADPH, as compared to an unmodified alcohol dehydrogenase.
68. The recombinant microorganism of embodiment 66, wherein the modified alcohol dehydrogenase exhibits an increased activity for reduction of acetone to isopropanol, as compared to an unmodified alcohol dehydrogenase.
69. The recombinant microorganism of embodiment 66, wherein the modified alcohol dehydrogenase exhibits an increased activity for oxidation of isopropanol to acetone, as compared to an unmodified alcohol dehydrogenase.
70. The recombinant microorganism of embodiments 68 or 69, wherein the modified alcohol dehydrogenase exhibits at least a 10 fold increase in activity with cofactor NADH as compared to an unmodified alcohol dehydrogenase.
71. The recombinant microorganism of embodiment 66, wherein the modified alcohol dehydrogenase shares at least 90% sequence identity with SEQ ID NO:2.
72. The recombinant microorganism of embodiment 66, wherein the modified alcohol dehydrogenase shares at least 95% sequence identity with SEQ ID NO:2.
73. The recombinant microorganism of embodiment 66, wherein the modified alcohol dehydrogenase shares at least 99% sequence identity with SEQ ID NO:2.
74. The recombinant microorganism of embodiment 66, wherein the alcohol dehydrogenase is a secondary alcohol dehydrogenase.
75. The recombinant microorganism of embodiment 66, wherein the modified alcohol dehydrogenase is a microbial alcohol dehydrogenase.
76. The recombinant microorganism of embodiment 75, wherein the microbial alcohol dehydrogenase is a bacterial alcohol dehydrogenase.
77. The recombinant microorganism of embodiment 76, wherein the bacterial alcohol dehydrogenase is a *Clostridium beijerinckii* alcohol dehydrogenase.
78. The recombinant microorganism of embodiment 66, wherein the polypeptide sequence comprises a signal peptide.
79. The recombinant microorganism of embodiment 66, wherein the signal peptide is a secretion signal.
80. The recombinant microorganism of embodiment 66, wherein the modified alcohol dehydrogenase sequence is selected from SEQ ID NOs: 3-38.
81. The recombinant microorganism of embodiment 66, wherein the modified alcohol dehydrogenase sequence comprises an amino acid substitution at one or more of the following residues: T38, G198, S199, Y218, I175, I173, R200, P201, C203, G244, E247, T248, K219, G243, Q251, Y267, L294, C295, K340, and K342.
82. The recombinant microorganism of embodiment 66, wherein the modified alcohol dehydrogenase sequence comprises an amino acid substitution at residue T38 with an H amino acid residue.
83. The recombinant microorganism of embodiment 66, wherein the modified alcohol dehydrogenase sequence comprises an amino acid substitution at residue G198 with a D, E, G, K, N, R, S, A, or V amino acid residue.
84. The recombinant microorganism of embodiment 66, wherein the modified alcohol dehydrogenase sequence comprises an amino acid substitution at residue S199 with a D, G, H, I, L, N, R, S, V, C, M, or P amino acid residue.
85. The recombinant microorganism of embodiment 66, wherein the modified alcohol dehydrogenase sequence comprises an amino acid substitution at residue Y218 with a P, A, D, F, I, N, S, T, V, Y, H, L, or Y amino acid residue.
86. The recombinant microorganism of embodiment 66, wherein the modified alcohol dehydrogenase sequence comprises an amino acid substitution at residue I173 with a V, T, A, L, T, F, or Y amino acid residue.
87. The recombinant microorganism of embodiment 66, wherein the modified alcohol dehydrogenase sequence comprises an amino acid substitution at residue I175 with a V or A amino acid residue.
88. The recombinant microorganism of embodiment 66, wherein the modified alcohol dehydrogenase sequence comprises an amino acid substitution at residue R200 with a R, G, S, or N amino acid residue.
89. The recombinant microorganism of embodiment 66, wherein the modified alcohol dehydrogenase sequence comprises an amino acid substitution at residue P201 with a P, E, D, K, or S amino acid residue.
90. The recombinant microorganism of embodiment 66, wherein the modified alcohol dehydrogenase sequence comprises an amino acid substitution at residue C203 with an R or K amino acid residue.
91. The recombinant microorganism of embodiment 66, wherein the modified alcohol dehydrogenase sequence comprises an amino acid substitution at residue G244 with an A, C, M, F, I, W, L, H, or P amino acid residue.
92. The recombinant microorganism of embodiment 66, wherein the modified alcohol dehydrogenase sequence comprises an amino acid substitution at residue E247 with a D, N, Q, or H amino acid residue.
93. The recombinant microorganism of embodiment 66, wherein the modified alcohol dehydrogenase sequence comprises an amino acid substitution at residue T248 with an S, N, A, L, M, or V amino acid residue.
94. The recombinant microorganism of embodiment 66, wherein the modified alcohol dehydrogenase sequence comprises one or more of the following amino acid substitutions: G198E, E247Q, E247D, E247N, Y218F, G198D, I173C, G198L, S199D, Y218P, or Y218A.
95. The recombinant microorganism of embodiment 66, wherein the modified alcohol dehydrogenase sequence comprises G198E and E247Q amino acid substitutions.
96. The recombinant microorganism of embodiment 66, wherein the modified alcohol dehydrogenase sequence comprises a G198E amino acid substitution.
97. The recombinant microorganism of embodiment 66, wherein the modified alcohol dehydrogenase sequence comprises G198E and Y218F amino acid substitutions.
98. The recombinant microorganism of embodiment 66, wherein the modified alcohol dehydrogenase sequence comprises G198E and E247D amino acid substitutions.
99. The recombinant microorganism of embodiment 66, wherein the modified alcohol dehydrogenase sequence comprises G198E and E247N amino acid substitutions.
100. The recombinant microorganism of embodiment 66, wherein the modified alcohol dehydrogenase sequence comprises G198D and Y218F amino acid substitutions.
101. The recombinant microorganism of embodiment 66, wherein the modified alcohol dehydrogenase sequence comprises I173C and G198E amino acid substitutions.
102. The recombinant microorganism of embodiment 66, wherein the modified alcohol dehydrogenase sequence comprises a G198D amino acid substitution.
103. The recombinant microorganism of embodiment 66, wherein the modified alcohol dehydrogenase sequence comprises G198L and S199D amino acid substitutions.
104. The recombinant microorganism of embodiment 66, wherein the modified alcohol dehydrogenase sequence comprises G198D and Y218P amino acid substitutions.
105. The recombinant microorganism of embodiment 66, wherein the modified alcohol dehydrogenase sequence comprises G198E and Y218P amino acid substitutions.
106. The recombinant microorganism of embodiment 66, wherein the modified alcohol dehydrogenase sequence comprises G198D and Y218A amino acid substitutions.
107. The recombinant microorganism of embodiment 66, wherein the modified alcohol dehydrogenase is NADH-dependent.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

While the disclosure is divided into sections, subsections, and further delineations, this is simply for exemplary purposes and is in no way intended to limit the methods, processes, compositions, products, substrates, media, and the like for use in any other aspect of the disclosure. For example, the disclosure of substrates used in the fermentation phase subsection does not limit the use of the substrates to fermentation phase processes.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A nucleic acid construct comprising a polynucleotide sequence encoding a modified alcohol dehydrogenase, wherein the alcohol dehydrogenase exhibits activity with cofactor NADH as compared to an unmodified alcohol dehydrogenase; and wherein the polynucleotide sequence shares at least 85% sequence identity with SEQ ID NO: 1; and wherein the amino acid sequence of the modified alcohol dehydrogenase is one of SEQ ID NO: 3, 5, 6, 7, 8, 9, 10, 12, 13, 14, 15, 16, 18, 19, 20, 21, 22, 25, 26, 28, 29, 30, 31, 32, 33, 34, 35, 36, and 37.

2. The nucleic acid construct of claim 1, wherein the modified alcohol dehydrogenase exhibits a cofactor preference for NADH over NADPH, as compared to the unmodified alcohol dehydrogenase.

3. The nucleic acid construct of claim 1, wherein the modified alcohol dehydrogenase exhibits an increased activity for reduction of acetone to isopropanol with NADH, as compared to the unmodified alcohol dehydrogenase.

4. The nucleic acid construct of claim 1, wherein the modified alcohol dehydrogenase exhibits an increased activity for oxidation of isopropanol to acetone, as compared to the unmodified alcohol dehydrogenase.

5. A method of producing a recombinant microorganism that produces a modified alcohol dehydrogenase that exhibits activity with cofactor NADH as compared to an unmodified alcohol dehydrogenase, the method comprising introducing a polynucleotide sequence encoding a modified alcohol dehydrogenase into a microorganism; wherein the modified alcohol dehydrogenase that exhibits activity with cofactor NADH as compared to the unmodified alcohol dehydrogenase; and wherein the amino acid sequence of the modified alcohol dehydrogenase is one of SEQ ID NO: 3, 5, 6, 7, 8, 9, 10, 12, 13, 14, 15, 16, 18, 19, 20, 21, 22, 25, 26, 28, 29, 30, 31, 32, 33, 34, 35, 36, and 37.

6. The method of claim 5, wherein the microorganism is a bacterium or a fungus.

7. The method of claim 5, wherein the modified alcohol dehydrogenase exhibits a cofactor preference for NADH over NADPH, as compared to the unmodified alcohol dehydrogenase.

8. A recombinant microorganism expressing a modified alcohol dehydrogenase that exhibits activity with cofactor NADH as compared to an unmodified alcohol dehydrogenase; and wherein the amino acid sequence of the modified alcohol dehydrogenase is one of SEQ ID NO: 3, 5, 6, 7, 8, 9, 10, 12, 13, 14, 15, 16, 18, 19, 20, 21, 22, 25, 26, 28, 29, 30, 31, 32, 33, 34, 35, 36, and 37.

9. The recombinant microorganism of claim 8, wherein the modified alcohol dehydrogenase exhibits a cofactor preference for NADH over NADPH, as compared to the unmodified alcohol dehydrogenase.

10. The nucleic acid construct of claim 1, wherein the amino acid sequence of the modified alcohol dehydrogenase is SEQ ID NO: 5.

11. The nucleic acid construct of claim 1, wherein the amino acid sequence of the modified alcohol dehydrogenase is one of SEQ ID NO: 14, 15, and 16.

12. The nucleic acid construct of claim 1, wherein the amino acid sequence of the modified alcohol dehydrogenase is SEQ ID NO: 29.

13. The nucleic acid construct of claim 1, wherein the amino acid sequence of the modified alcohol dehydrogenase is SEQ ID NO: 35.

14. The method of claim 5, wherein the amino acid sequence of the modified alcohol dehydrogenase is SEQ ID NO: 5.

15. The method of claim 5, wherein the amino acid sequence of the modified alcohol dehydrogenase is one of SEQ ID NO: 14, 15, and 16.

16. The method of claim 5, wherein the amino acid sequence of the modified alcohol dehydrogenase is SEQ ID NO: 29.

17. The method of claim 5, wherein the amino acid sequence of the modified alcohol dehydrogenase is SEQ ID NO: 35.

18. The recombinant microorganism of claim 8, wherein the amino acid sequence of the modified alcohol dehydrogenase is SEQ ID NO: 5.

19. The recombinant microorganism of claim 8, wherein the amino acid sequence of the modified alcohol dehydrogenase is one of SEQ ID NO: 14, 15, and 16.

20. The recombinant microorganism of claim 8, wherein the amino acid sequence of the modified alcohol dehydrogenase is one of SEQ ID NO: 29 and 35.

* * * * *